US009920380B2

(12) United States Patent
Dimitrov et al.

(10) Patent No.: US 9,920,380 B2
(45) Date of Patent: *Mar. 20, 2018

(54) METHODS FOR DETECTION AND QUANTIFICATION OF ANALYTES IN COMPLEX MIXTURES

(71) Applicant: The Institute for Systems Biology, Seattle, WA (US)

(72) Inventors: Krassen M. Dimitrov, Seattle, WA (US); Dwayne L. Dunaway, Seattle, WA (US)

(73) Assignee: The Institute for Systems Biology, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/794,299

(22) Filed: Mar. 11, 2013

(65) Prior Publication Data
US 2014/0162251 A1 Jun. 12, 2014

Related U.S. Application Data

(63) Continuation of application No. 13/027,493, filed on Feb. 15, 2011, now Pat. No. 8,492,094, which is a continuation of application No. 10/542,458, filed as application No. PCT/US02/21278 on Jul. 3, 2002, now Pat. No. 7,919,237, which is a continuation-in-part of application No. 09/898,743, filed on Jul. 3, 2001, now Pat. No. 7,473,767.

(51) Int. Cl.
*C12Q 1/68* (2006.01)
(52) U.S. Cl.
CPC .......... *C12Q 1/6888* (2013.01); *C12Q 1/682* (2013.01); *C12Q 1/6816* (2013.01); *C12Q 1/6876* (2013.01)

(58) Field of Classification Search
None
See application file for complete search history.

(56) References Cited

U.S. PATENT DOCUMENTS

| 4,716,106 | A  | 12/1987 | Chiswell |
| 4,824,775 | A  | 4/1989  | Dattagupta et al. |
| 5,124,246 | A  | 6/1992  | Urdea et al. |
| 5,293,050 | A  | 3/1994  | Chapple-Sokol et al. |
| 5,320,814 | A  | 6/1994  | Walt et al. |
| 5,354,707 | A  | 10/1994 | Chapple-Sokol et al. |
| 5,401,847 | A  | 3/1995  | Glazer et al. |
| 5,487,973 | A  | 1/1996  | Nilsen et al. |
| 5,543,838 | A  | 8/1996  | Hosier et al. |
| 5,679,519 | A  | 10/1997 | Oprandy |
| 5,707,797 | A  | 1/1998  | Windle |
| 5,853,993 | A  | 12/1998 | Dellinger et al. |
| 5,981,180 | A  | 11/1999 | Chandler et al. |
| 6,027,889 | A  | 2/2000  | Barany et al. |
| 6,207,392 | B1 | 3/2001  | Weiss et al. |
| 6,261,779 | B1 | 7/2001  | Barbera-Guillem et al. |
| 6,268,148 | B1 | 7/2001  | Barany et al. |
| 6,277,583 | B1 | 8/2001  | Krantz et al. |
| 6,312,892 | B1 | 11/2001 | Barany et al. |
| 6,361,944 | B1 | 3/2002  | Mirkin et al. |
| 6,417,340 | B1 | 7/2002  | Mirkin et al. |
| 6,428,667 | B1 | 8/2002  | Glazer et al. |
| 6,429,027 | B1 | 8/2002  | Chee et al. |
| 6,465,175 | B2 | 10/2002 | Horn et al. |
| 6,495,324 | B1 | 12/2002 | Mirkin et al. |
| 6,506,564 | B1 | 1/2003  | Mirkin et al. |
| 6,506,594 | B1 | 1/2003  | Barany et al. |
| 6,534,266 | B1 | 3/2003  | Singer |
| 6,534,293 | B1 | 3/2003  | Barany et al. |
| 6,537,755 | B1 | 3/2003  | Drmanac |

(Continued)

FOREIGN PATENT DOCUMENTS

| EP | 0292128 A1 | 11/1988 |
| EP | 1006200 A2 | 6/2000 |

(Continued)

OTHER PUBLICATIONS

Luehrsen, K. et al. High-density hapten labelling and HRP conjugation of oligonucleotides for use as in situ hybridization probes to detect mRNA targets in cells and tissues. The J. Histochem. & Cytochem., vol. 48(1), p. 133-145, 2000.*
Tanke et al. New Strategy for multi-color fluorescence in situ hybridization: COBRA: combined binary RAtio labelling. European J Human Genetics. vol. 7, p. 2-11, 1999.*
Asbury et al., "Trapping of DNA in Nonuniform Oscillating Electric Fields", *Biophys. J.*, 74:1024-1030 (1998).
Bonetta, L., "Gene expression: one size does not fit all", *Nature Meth.*, 3(5):401-409 (2006).
Brenner et al., "Gene expression analysis by massively parallel signature sequencing (MPSS) on microbead arrays", *Nature Biotech.*, 18(6):630-634 (2000).

(Continued)

*Primary Examiner* — Prabha Chunduru
(74) *Attorney, Agent, or Firm* — Cooley LLP; Ivor R. Elrifi; Matthew Pavao

(57) ABSTRACT

The invention provides a diverse population of uniquely labeled probes, containing about thirty or more target specific nucleic acid probes each attached to a unique label bound to a nucleic acid. Also provided is a method of producing a population of uniquely labeled nucleic acid probes. Also provided is a method of detecting a nucleic acid analyte. The method consists of (a) contacting a mixture of nucleic acid analytes under conditions sufficient for hybridization with a plurality of target specific nucleic acid probes each having a different specifier; (b) contacting the mixture under conditions sufficient for hybridization with a corresponding plurality of anti-genedigits each having a unique label, the plurality of anti-genedigits having a diversity sufficient to uniquely hybridize to genedigits within the specifiers, and (c) uniquely detecting a hybridized complex between one or more analytes in the mixture, a target specific probe, and an anti-genedigit.

17 Claims, 5 Drawing Sheets

(56) References Cited

U.S. PATENT DOCUMENTS

| | | | |
|---|---|---|---|
| 6,582,921 B2 | 6/2003 | Mirkin et al. | |
| 6,610,491 B2 | 8/2003 | Mirkin et al. | |
| 6,645,721 B2 | 11/2003 | Mirkin et al. | |
| 6,673,548 B2 | 1/2004 | Mirkin et al. | |
| 6,677,122 B2 | 1/2004 | Mirkin et al. | |
| 6,682,895 B2 | 1/2004 | Mirkin et al. | |
| 6,750,016 B2 | 6/2004 | Mirkin et al. | |
| 6,767,702 B2 | 7/2004 | Mirkin et al. | |
| 6,797,470 B2 | 9/2004 | Barany et al. | |
| 6,942,968 B1* | 9/2005 | Dickinson | B01J 19/0046 435/174 |
| 7,473,767 B2* | 1/2009 | Dimitrov | 536/23.1 |
| 7,919,237 B2* | 4/2011 | Dimitrov et al. | 435/6.1 |
| 8,148,512 B2 | 4/2012 | Dimitrov | |
| 8,492,094 B2* | 7/2013 | Dimitrov et al. | 435/6.12 |
| 9,046,477 B2 | 6/2015 | Emedcoles et al. | |
| 9,228,948 B2 | 1/2016 | Emedcoles et al. | |
| 9,297,762 B2 | 3/2016 | Emedcoles et al. | |
| 9,304,084 B2 | 4/2016 | Emedcoles et al. | |
| 2001/0002315 A1 | 5/2001 | Schultz et al. | |
| 2001/0007775 A1 | 7/2001 | Seul et al. | |
| 2001/0023078 A1 | 9/2001 | Bawendi et al. | |
| 2001/0029049 A1 | 10/2001 | Walt et al. | |
| 2001/0034034 A1 | 10/2001 | Bruchez et al. | |
| 2001/0053334 A1 | 12/2001 | Chen et al. | |
| 2002/0009728 A1 | 1/2002 | Bittner et al. | |
| 2002/0028457 A1 | 3/2002 | Empedocles et al. | |
| 2002/0034737 A1 | 3/2002 | Drmanac | |
| 2002/0034827 A1 | 3/2002 | Singh et al. | |
| 2002/0051971 A1 | 5/2002 | Stuelpnagel et al. | |
| 2002/0068018 A1 | 6/2002 | Pepper et al. | |
| 2002/0150921 A1 | 10/2002 | Barany et al. | |
| 2002/0177141 A1 | 11/2002 | Chee et al. | |
| 2002/0187515 A1 | 12/2002 | Chee et al. | |
| 2002/0192687 A1 | 12/2002 | Mirkin et al. | |
| 2003/0008323 A1 | 1/2003 | Ravkin et al. | |
| 2003/0022182 A1 | 1/2003 | Barany et al. | |
| 2003/0028981 A1* | 2/2003 | Chandler | C12Q 1/6816 8/607 |
| 2003/0032016 A1 | 2/2003 | Barany et al. | |
| 2003/0077635 A1 | 4/2003 | Lohse | |
| 2003/0082545 A1 | 5/2003 | Barany et al. | |
| 2003/0087242 A1 | 5/2003 | Mirkin et al. | |
| 2003/0175750 A1 | 9/2003 | Barany et al. | |
| 2003/0186426 A1 | 10/2003 | Brewer et al. | |
| 2003/0190634 A1 | 10/2003 | Barany et al. | |
| 2004/0048308 A1 | 3/2004 | Barany et al. | |
| 2004/0203061 A1 | 10/2004 | Barany et al. | |
| 2004/0214224 A1 | 10/2004 | Barany et al. | |
| 2005/0233318 A1 | 10/2005 | Chee et al. | |
| 2007/0166708 A1 | 7/2007 | Dimitrov et al. | |

FOREIGN PATENT DOCUMENTS

| | | |
|---|---|---|
| WO | WO-9707245 | 2/1997 |
| WO | WO-9714028 | 4/1997 |
| WO | WO-9804740 A1 | 2/1998 |
| WO | WO-9918434 | 4/1999 |
| WO | WO-9919515 A1 | 4/1999 |
| WO | WO-9937814 A1 | 7/1999 |
| WO | WO-9947643 A1 | 9/1999 |
| WO | WO-9952708 A1 | 10/1999 |
| WO | WO-9962926 A1 | 12/1999 |
| WO | WO-200073777 | 12/2000 |
| WO | WO-200100875 | 1/2001 |
| WO | WO-0222889 A2 | 3/2002 |
| WO | WO-02056014 A2 | 7/2002 |
| WO | WO-02079490 A2 | 10/2002 |

OTHER PUBLICATIONS

Chen et al., "A Microsphere-Based Assay for Multiplexed Single Nucleotide Polymorphism Analysis Using Single Base Chain Extension", *Genome Res.*, 10(4):549-557 (2000).

Chen et al., "Homogeneous genotyping assays for single nucleotide polymorphisms with fluorescence resonance energy transfer detection", *Genet. Anal.*, 14:157-163 (1999).

Collins et al., "A branched DNA signal amplification assay for quantification of nucleic acid targets below 100 molecules/ml", *Nucl. Acids Res.*, 25(15):2979-2984 (1997).

Cramer et al., "Using fluorescence resonance energy transfer (FRET) for measuring 2-5A analogues ability to activate RNase L", *Nucleosides Nucleotides*, 18(6&7):1523-1525 (1999).

Dauwerse et al., "Multiple colors by fluorescence in situ hybridization using ratio-labelled DNA probes create molecular karyotype", *Human Molec. Genet.*, 1(8):593-598 (1992).

Deniz et al., "Single-pair fluorescence resonance energy transfer on freely diffusing molecules: observation of Forster distance dependence and subpopulations", *Proc. Natl. Acad. Sci. U.S.A.*, 96(7):3670-3675 (1999).

Empedocles et al., "Nanocrystals: A new material for high-sensitivity, multicolor bioassays", (Abstract No. 212), *Abstracts of Papers Amer. Chem. Soc.*, 219:212 (2000).

Empedocles et al., "Photoluminescence from Single Semiconductor Nanostructures", *Adv. Mat.*, 11(15):1243-1256 (1999).

Fan et al., "Parallel Genotyping of Human SNPs Using Generic High-density Oligonucleotide Tag Arrays", *Genome Res.*, 10(6):853-860 (2000).

Geselowitz et al., "Fluorescence resonance energy transfer analysis of RNase L-catalyzed oligonucleotide cleavage", *Antisense Nucleic Acid Drug Dev.*, 10(1):45-51 (2000).

Henegariu et al., "Rapid DNA Fiber Technique for Size Measurements of Linear and Circular DNA Probes", *BioTech.*, 31(2):246-250 (2001).

Hirschhorn et al., "SBE-TAGS: An array-based method for efficient single-nucleotide polymorphism genotyping", *Proc. Natl. Acad. Sci. U.S.A.*, 97(22):12164-12169 (2000).

Hodak et al., "Photophysics of Nanometer Sized Metal Particles: Electron-Phonon Coupling and Coherent Excitation of Breathing Vibrational Modes", *J. Phys. Chem.*, 104(43):9954-9965 (2000).

Horn et al., "Forks and combs and DNA: the synthesis of branched oligodeoxyribonucleotides", *Nucl. Acids Res.*, 17(17):6959-6957 (1989).

Jayasena, S. D., "Aptamers: An Emerging Class of Molecules That Rival Antibodies in Diagnostics", *Clin. Chem.*, 45(9):1628-1650 (1999).

Luehrsen et al., "High-density hapten labeling and HRP conjugation of oligonucleotides for use as in situ hybridization probes to detect mRNA targets in cells and tissues", *J. Histochem. Cytochem.*, 48(1):133-145 (2000).

Malik et al., "Semiconductor nanoparticles: their properties, synthesis and potential for application", *South African J. Sci.*, 96(2):55-60 (2000).

Matsuura et al., "Real-time observation of a single DNA digestion by λ exonuclease under a fluorescence microscope field", *Nucl. Acids Res.*, 29(16):E79 (2001) (5 pages).

Morrison et al., "Two-Color Ratio-Coding of Chromosome Targets in Fluorescence In Situ Hybridization: Quantitative Analysis and Reproducibility", *Cytometry*, 27:314-326 (1997).

Nederlof et al., "Fluorescence Ratio Measurements of Double-Labeled Probes for Multiple In Situ Hybridization by Digital Imaging Microscopy", *Cytometry*, 13:839-845 (1992).

Penner, R. M., "Hybrid Electrochemical/Chemical Synthesis of Quantum Dots," *Acc. Chem. Res.*, 33(2):78-86 (2000).

Tanke et al., "New strategy for multi-colour fluorescence in situ hybridization: COBRA: Combined Binary Ratio labelling", *Eur. J. Human Genetics*, 7:2-11 (1999).

Tong et al., "Combinatorial fluorescence energy transfer tags for multiplex biological assays", *Nature Biotech.*, 19(8):756-759 (2001).

Toth et al., "DNA Curvature in Solution Measured by Fluorescence Resonance Energy Transfer", *Biochem.*, 37(22):8173-8179 (1998).

Vitiello et al., "Intracellular ribozyme-catalyzed trans-cleavage of RNA monitored by fluorescence resonance energy transfer", *RNA*, 6(4):628-637 (2000).

Wang et al., "Phosphate-Specific Fluorescence Labeling under Aqueous Conditions", *Anal. Chem.*, 65:3518-3520 (1993).

(56) References Cited

OTHER PUBLICATIONS

Wong et al., "Detection of Single-nucleotide Polymorphism and Expression Analysis using Microspheres Encoded with Quantum Dot Semiconductor Nanocrystals", *Am. J. Hum. Genet.*, 67(4):458 (2000).

Yokota et al., "A new method for straightening DNA molecules for optical restriction mapping", *Nucl. Acids Res.*, 25(5):1064-1070 (1997).

Alfano et al., "Optical Sensing, Imaging,and Manipulation for Biological and biomedical applications" SPIE—The International Society for Optical Engineering, Jul. 2000, vol. 4082, Taiwan.

Ferguson et al., "High-Density Fiber-Optic DNA Random Microsphere Array" *Analytical Chemistry* 72 (22), 5618-5624 (2000).

Steemers et al., "Screening unlabeled DNA targets with randomly ordered fiber-optic gene arrays." *Nature Biotechnology*. 18, 91-94 (2000).

Werner et al., "Current status of DNA sequencing by single molecule detection" Proc. SPIE 3602, Advances in Fluorescence Sensing Technology IV, 355, (1999).

\* cited by examiner

METHODS FOR DETECTION AND QUANTIFICATION OF ANALYTES IN COMPLEX MIXTURES

RELATED APPLICATIONS

This application is a continuation of U.S. Utility application Ser. No. 13/027,493, filed Feb. 15, 2011, now U.S. Pat. No. 8,492,094, which is a continuation of U.S. Utility application Ser. No. 10/542,458, now U.S. Pat. No. 7,919,237, filed Jan. 26, 2007, which entered the national stage under 35 U.S.C. 371 and corresponds to International Application No. PCT/US2002/021278, filed Jul. 3, 2002, which is a continuation-in-part of U.S. Utility application Ser. No. 09/898,743, filed Jul. 3, 2001, now U.S. Pat. No. 7,473,767, the contents of each of which are each herein incorporated by reference in their entireties.

INCORPORATION OF SEQUENCE LISTING

The contents of the text file named "40448-501C03US ST25.txt," which was created on May 3, 2013 and is 2 KB in size, are hereby incorporated by reference in their entirety.

BACKGROUND OF THE INVENTION

This invention relates generally to the field of genomics and, more specifically to detection, identification, and quantification of target analytes in mixtures.

Although all cells in the human body contain the same genetic material, the same genes are not active in all of those cells. Alterations in gene expression patterns can have profound effects on biological functions. These variations in gene expression are at the core of altered physiologic and pathologic processes. Therefore, identifying and quantifying the expression of genes in normal cells compared to diseased cells can aid the discovery of new drug and diagnostic targets.

Nucleic acids can be detected and quantified based on their specific polynucleotide sequences. The basic principle underlying existing methods of detection and quantification is the hybridization of a labeled complementary probe sequence to a target sequence of interest in a sample. The formation of a duplex indicates the presence of the target sequence in the sample and the degree of duplex formation, as measured by the amount of label incorporated in it, is proportional to the amount of the target sequence.

This technique, called molecular hybridization, has been a useful tool for identifying and analyzing specific nucleic acid sequences in complex mixtures. This technique has been used in diagnostics, for example, to detect nucleic acid sequences of various microbes in biological samples. In addition, hybridization techniques have been used to map genetic differences or polymorphisms between individuals. Furthermore, these techniques have been used to monitor changes in gene expression in different populations of cells or in cells treated with different agents.

In the past, only a few genes could be detected in a complex sample at one time. However, DNA microarrays, devices that consist of thousands of immobilized DNA sequences present on a miniaturized surface, have made this process more efficient. Using a microarray, it is possible in a single experiment to detect the presence or absence of thousands of genes in a biological sample. This allows researchers to simultaneously perform several diagnostic tests on one sample, or to observe expression level changes in thousands of genes in one experiment. Generally, microarrays are prepared by binding DNA sequences to a surface such as a nylon membrane or glass slide at precisely defined locations on a grid. Then nucleic acids in a biological sample are labeled and hybridized to the array. The labeled sample DNA marks the exact position on the array where hybridization occurs, allowing automatic detection.

Unfortunately, despite the miniaturization of array formats, this method still requires significant amounts of the biological sample. However, in several cases, such as biopsies of diseased tissues or samples of a discrete cell type, the biological sample is in limited supply. In addition, the kinetics of hybridization on the surface of a microarray is less efficient than hybridization in small amounts of aqueous solution. Furthermore, microarrays require a large dynamic range of detection to account for large difference in abundance of the different molecular species. This results in decreased sensitivity since there is a trade-off between sensitivity and dynamic range. A further problem with microarray methods is that the output is quantitative analog data that has undergone several intermediary transformations. In microarrays, the amount of nucleic acid hybridized to each spot is determined by measuring its label and so any nonlinear correlation between the amount of DNA hybridized and the amount of the label detected will skew the data output. Such non-linearity has been widely documented.

Thus, there exists a need for accurate and sensitive detection, identification and quantification of analytes in complex mixtures. The present invention satisfies this need and provides related advantages as well.

SUMMARY OF THE INVENTION

The invention provides a diverse population of uniquely labeled probes, containing about thirty or more target specific nucleic acid probes each attached to a unique label bound to a nucleic acid. Also provided is a method of producing a population of uniquely labeled nucleic acid probes. The method consists of (a) synthesizing a population of target specific nucleic acid probes each having a different specifier; (b) synthesizing a corresponding population of anti-genedigits each having a unique label, the population having a diversity sufficient to uniquely hybridize to genedigits within the specifiers, and (c) hybridizing the populations of target nucleic acid probes to the anti-genedigits, to produce a population in which each of the target specific probes is uniquely labeled. Also provided is a method of detecting a nucleic acid analyte. The method consists of (a) contacting a mixture of nucleic acid analytes under conditions sufficient for hybridization with a plurality of target specific nucleic acid probes each having a different specifier; (b) contacting the mixture under conditions sufficient for hybridization with a corresponding plurality of anti-genedigits each having a unique label, the plurality of anti-genedigits having a diversity sufficient to uniquely hybridize to genedigits within the specifiers, and (c) uniquely detecting a hybridized complex between one or more analytes in the mixture, a target specific probe, and an anti-genedigit.

BRIEF DESCRIPTION OF THE DRAWINGS

FIG. 1 shows components of a specifier.

FIG. 4B shows the labeled DNA probe molecule that have been aligned in the flow cell with the voltage on.

DETAILED DESCRIPTION OF THE INVENTION

Figure 1A:
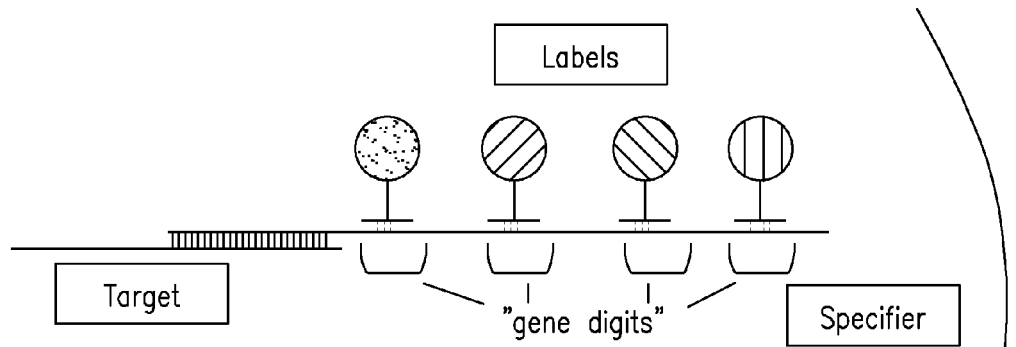
FIG. 1A shows an association between a target and a labeled specifier.

This invention is directed to methods for the generation of a diverse population of unique labels that can be used for the detection, identification, and direct quantification of a wide variety of target analytes. The methods are advantageous in that they generate a large number of unique labels of about the same unit signal starting from just a small number of different labels. Enough labels are generated by this method so that each analyte in a complex mixture can be uniquely bound by a label and thus identified. The labels are designed so that they can be used in a small volume of solution which increases the efficiency of the binding reaction and is useful when only small amounts of sample are available for analysis. After the individual molecules in a sample are identified, they can be directly counted resulting in a digital read-out of each molecular species in a mixture. Since the diverse labels are based on a small number of starting labels, this allows the detection method to operate in a narrow dynamic range resulting in improved sensitivity of the system since the trade-off between sensitivity and dynamic range is avoided. The methods of the invention therefore provide an accurate and sensitive system for the detection, identification and quantitation of analytes in a mixture.

In one embodiment, the invention is directed to detecting nucleic acid analytes in a complex mixture by first contacting the mixture under conditions sufficient for hybridization with a plurality of target specific nucleic acid probes. These target specific nucleic acid probes, called specifiers, contain a target specific region and a region containing one or more unique "genedigit" sequences. The genedigits consist of repeated core element sequences that can be specifically bound by a complementary anti-genedigit sequence which can contain a unique label. The mixture containing the nucleic acid analytes and the specifiers is then contacted with a corresponding plurality of labeled anti-genedigits having a diversity sufficient to uniquely hybridize to genedigits within the specifiers. This allows the unique detection of a hybridized complex between analytes in the mixture and specifiers with unique labels.

As used herein, the term "bound" when referring to a unique label or nucleic acid is intended to mean that a label monomer is attached to a nucleotide in a 1:1 correspondence. A label monomer as used herein is intended to mean an individual measurable moiety, such as a radioisotope, fluorochrome, dye, enzyme, nanoparticle, chemiluminescent marker, biotin, or other moiety known in the art that is measurable by analytical methods. A label monomer can be directly attached to a nucleotide using methods well known in the art. Nucleotides can also be chemically modified or derivitized in order to attach a label monomer. For example, a fluorescent monomer such as a fluorescein molecule can be attached to dUTP (deoxyuridine-triphosphate) using a four-atom aminoalkynyl group. Each label monomer is attached to a nucleotide making a label monomer:nucleotide complex. This label monomer:nucleotide can be incorporated into nucleic acids in a variety of ways. For example, a label monomer:nucleotide can be incorporated at only one location within a nucleic acid or at two or more locations within a nucleic acid. A nucleotide can be attached to a label monomer first and then be incorporated into a nucleic acid, or an existing nucleic acid can be labeled by attaching a label monomer to a nucleotide within the nucleic acid. In addition, for example, a label monomer:nucleotide can be incorporated into a nucleic acid and a different type of label monomer:nucleotide can be incorporated into the same nucleic acid.

As used herein, "analyte" or target when referring to an analyte is intended to mean any molecule whose presence is measured. An analyte molecule can be essentially any molecule for which a detectable probe or assay exists or can be produced by one skilled in the art. For example, an analyte can be a macromolecule such as a nucleic acid, polypeptide or carbohydrate, or a small organic compound. Measurement can be quantitative or qualitative. An analyte can be part of a sample that contains other components or can be the sole or major component of the sample. Therefore, an analyte can be a component of a whole cell or tissue, a cell or tissue extract, a fractionated lysate thereof or a substantially purified molecule. The analyte can be attached in solution or solid-phase, including, for example, to a solid surface such as a chip, microarray or bead. Also the analyte can have either a known or unknown structure or sequence.

As used herein, the term "target specific" is intended to mean an agent that binds to a target analyte selectively. This agent will bind with preferential affinity toward the target while showing little to no detectable cross-reactivity toward other molecules. For example, when the target is a nucleic acid, a target specific sequence is one that is complementary to the sequence of the target and able to hybridize to the target sequence with little to no detectable cross-reactivity with other nucleic acid molecules. A nucleic acid target could also be bound in a target specific manner by a protein, for example by the DNA binding domain of a transcription factor. If the target is a protein or peptide it can be bound specifically by a nucleic acid aptamer, or another protein or peptide, or by an antibody or antibody fragment which are sub-classes of proteins.

The term "complementary" refers to two nucleotides that can form multiple thermodynamically favorable interactions with one another. For example, adenine is complementary to thymine as they can form two hydrogen bonds. Similarly, guanine and cytosine are complementary since they can form three hydrogen bonds. A nucleotide sequence is the complement of another nucleotide sequence if the nucleotides of the first sequence are complementary to the nucleotides of the second sequence. The percent of complementarity (i.e. how many nucleotides from one strand form multiple thermodynamically favorable interactions with the other strand compared with the total number of nucleotides present in the sequence) indicates the extent of complementarity of two sequences.

As used herein, the term "repeat sequence" is intended to mean two or more copies of a core element. A repeat sequence can have direct repetition of the core sequence without any intervening sequence, or the repeat sequence can have non-consecutive repetition of the core element with intervening sequences. A core element can be made of nucleic acids such as an oligonucleotide or an aptamer, or the core element can be made of amino acids such as a peptide sequence. If, for example, the core element is a nucleic acid sequence of 8 base pairs then three direct repeats of this sequence would be a 24 base sequence. A "complimentary repeat sequence" is a sequence that binds specifically to the repeat sequence. For the example above where the repeat sequence is repetition of a nucleic acid core element, the complimentary repeat sequence can contain one or more copies of the complementary strand of the core element that will hybridize specifically to the repeat sequence.

As used herein, the term "genedigit" is intended to mean a region of pre-determined nucleotide or amino acid sequence that serves as an attachment point for a label. The genedigit can have any structure including, for example, a single unique sequence or a sequence containing repeated core elements. Each genedigit has a unique sequence which differentiates it from other genedigits. An "anti-genedigit" is a nucleotide or amino acid sequence or structure that binds specifically to the gene digit. For example, if the genedigit is a nucleic acid, the anti-genedigit can be a nucleic acid sequence that is complementary to the genedigit sequence. If the genedigit is a nucleic acid that contains repeated core elements then the anti-genedigit can be a series of repeat sequences that are complementary to the repeat sequences in the genedigit. An anti-genedigit can contain the same number, or a lesser number, of repeat sequences compared to the genedigit as long as the anti-genedigit is able to specifically bind to the genedigit.

As used herein, the term "specifier" is intended to mean the linkage of one or more genedigits to a target specific sequence. The genedigits can be directly linked or can be attached using an intervening or adapting sequence. A specifier can contain a target specific sequence which will allow it to bind to a target analyate. An "anti-specifier" has a complementary sequence to all or part of the specifier such that it specifically binds to the specifier.

As used herein, the term "mixture" is intended to mean a composition that contains more than one molecule. A mixture can be homogenous, containing a single species, or heterogeneous, containing different species. Examples of homogeneous samples include, for example, isolated populations of polypeptides, nucleic acids or carbohydrates. Heterogeneous mixtures include extracts from tissues, cells, lysates and fractionated portions thereof. For example, a mixture can be a pure solution containing several molecules of a single protein, or a mixture can be an extract from a cell containing several proteins and other types of macromolecules.

As used herein, the term "label" is intended to mean a molecule or molecules that render an analyte detectable by an analytical method. An appropriate label depends on the particular assay format and are well known by those skilled in the art. For example, a label specific for a nucleic acid molecule can be a complementary nucleic acid molecule attached to a label monomer or measurable moiety, such as a radioisotope, fluorochrome, dye, enzyme, nanoparticle, chemiluminescent marker, biotin, or other moiety known in the art that is measurable by analytical methods. In addition, a label can include any combination of label monomers.

As used herein, "unique" when used in reference to label is intended to mean a label that has a detectable signal that distinguishes it from other labels in the same mixture. Therefore, a unique label is a relative term since it is dependent upon the other labels that are present in the mixture and the sensitivity of the detection equipment that is used. In the case of a fluorescent label, a unique label is a label that has spectral properties that significantly differentiate it from other fluorescent labels in the same mixture. For example, a fluorescein label can be a unique label if it is included in a mixture that contains a rhodamine label since these fluorescent labels emit light at distinct, essentially non-overlapping wavelengths. However, if another fluorescent label was added to the mixture that emitted light at the same or very similar wavelength to fluorescein, for example the Oregon Green fluorophore, then the fluorescein would no longer be a unique label since Oregon Green and fluorescein could not be distinguished from each other. A unique label is also relative to the sensitivity of the detection equipment used. For example, a FACS machine can be used to detect the emission peaks from different fluorophore-containing labels. If a particular set of labels have emission peaks that are separated by, for example, 2 nm these labels would not be unique if detected on a FACS machine that can distinguish peaks that are separated by 10 nm or greater, but these labels would be unique if detected on a FACS machine that can distinguish peaks separated by 1 nm or greater.

As used herein, the term "signal" is intended to mean a detectable, physical quantity or impulse by which information on the presence of an analyte can be determined. Therefore, a signal is the read-out or measurable component of detection. A signal includes, for example, fluorescence, luminescence, calorimetric, density, image, sound, voltage, current, magnetic field and mass. Therefore, the term "unit signal," as used herein is intended to mean a specified quantity of a signal in terms of which the magnitudes of other quantities of signals of the same kind can be stated. Detection equipment can count signals of the same type and display the amount of signal in terms of a common unit. For example, a nucleic acid can be radioactively labeled at one nucleotide position and another nucleic acid can be radioactively labeled at three nucleotide positions. The radioactive particles emitted by each nucleic acid can be detected and quantified, for example in a scintillation counter, and displayed as the number of counts per minute (cpm). The nucleic acid labeled at three positions will emit about three times the number of radioactive particles as the nucleic acid labeled at one position and hence about three times the number of cpms will be recorded.

As used herein, the term "dendrimer" is intended to mean a branched nucleic acid. These structures are composed of layers of nucleic acid, each layer being composed of partially single-stranded heteroduplexes which are called dendrimer monomers. The outermost layer of a given dendrimer can have multiple single-stranded arms capable of hybridization with a complementary nucleic acid sequence. Dendrimer monomers have the property that sequential addition of monomers yields a three-dimensional structure composed of nucleic acid. Various configurations of nucleic acid molecules can give rise to a large number of differently shaped dendritic structures. For example, using commercially available dendrimeric synthons, a dendrimer with 1 stem and 81 branches can be synthesized. Also fork-like, comb-like and bubbled structures are possible.

As used herein, the term "nucleic acid" is intended to mean a single- or double-stranded DNA or RNA molecule including, for example, genomic DNA, cDNA and mRNA. The term is intended to include nucleic acid molecules of both synthetic and natural origin. A nucleic acid molecule of the invention can be of linear, circular or branched configuration, and can represent either the sense or antisense strand, or both, of a native nucleic acid molecule. A nucleic acid molecule of the invention can further incorporate a detectable moiety such as a radiolabel, a fluorochrome, a ferromagnetic substance, a luminescent tag or a detectable moiety such as biotin.

As used herein, the term "hybridizing" is intended to mean joining different components together. Any number of components can be joined together, for example two components can be joined together to make a duplex, three components can be joined together to make a triplex, and so on. Nucleic acids can form a hybrid or duplex, for example, by hydrogen bonding between complementary nucleotides. The formation of nucleic acid hybrids is dependent on several conditions known in the art, including temperature, salt concentration, and pH.

As used herein, "complexity" refers to the degree of repeated elements between two nucleic acids that are being hybridized together in a solution (see Anderson, M. L. M., *Nucleic Acid Hybridization*, Springer-Verlag, New York (1999)). When the nucleic acid molecules that are to be hybridized contain repeated core elements or homopolymeric regions, there are many possible pairing opportunities and so the hybridization proceeds quickly. When the nucleic acid molecules that are to be hybridized do not contain any repeated core elements then there is only one way that the two sequences can be hybridized and so the hybridization proceeds more slowly. Sequences that hybridize quickly are said to have a low complexity, while sequences that take longer to hybridize have a higher complexity. For example, a 40 base pair genedigit sequence made up of five direct repeats of an 8 base pair core element, can be hybridized to a 24 base pair anti-genedigit containing three repeats of the 8 base pair core repeat in three different registers (see, for example, FIG. 1C). Thus the anti-genedigit can hybridize to the 40 base pair genedigit through a 24 base pair sequence that only has a complexity of an 8 base pair sequence.

The invention provides a diverse population of labels and methods for generating a large number of unique labels of about the same unit signal starting from just a small number of different labels. Enough labels are generated by this method so that each analyte in a complex mixture can be uniquely bound by a label and thus identified. These labels can be used in very small volumes which improves kinetics in the binding reaction. In addition, the design of these labels allows for improved accuracy in detection.

A large diversity of unique labels can be desirable in order to provide a unique label to each species in a complex mixture. The invention provides methods for combining different labels in pre-determined ratios to generate a large diversity of unique labels. The labels are designed in a modular fashion which allows for flexibility in the number of unique labels that are generated. For example, if a large number of modules are used, a large number of ratios of the different labels is possible which leads to a large number of unique labels. The number of labels generated can be adjusted to cover mixtures with different numbers of species.

The invention provides a diverse population of labels that contains thirty or more unique labels where each unique label is bound to a nucleic acid. A diverse population of labels is a mixture of distinct label species. This population can have as few as about thirty distinct label species or as high as $10^{17}$ distinct label species. The actual number of molecules of each label species can vary as long as at least one molecule of the label species is present. In addition, the invention provides a diverse population of labels that contains 40, 60, 80, 100, 120, 140, or about 150 unique labels. A portion of this population can be made up of different individual label monomers. The invention also provides unique labels made from combinations of different labels which can increase the number of unique labels substantially.

The labels of the invention are bound to nucleic acids. In particular, the labels are bound to nucleic acids through the attachment of a label monomer to a nucleotide within a nucleic acid in a 1:1 correspondence. A nucleic acid can contain several label monomers, however each label monomer is attached directly to a nucleotide.

A label monomer can be attached to any nucleotide including both natural and non-natural nucleotides. A nucleotide contains three parts, a phosphate group, a pentose five-carbon sugar molecule, and an organic base. In RNA, the pentose is ribose and in DNA it is deoxyribose and so nucleotides for incorporation into RNA are called ribonucleotides and nucleotides for incorporation into DNA are called deoxyribonucleotides. Three bases adenine, guanine, and cytosine are found in both DNA and RNA while thymine is normally found only in DNA and uracil is normally found only in RNA. Nucleotides can have one, two or three attached phosphate groups and are sometimes referred to as nucleoside phosphates. Nucleotides can contain modified nucleosides having modified bases (e.g., 5-methyl cytosine) and modified sugar groups (e.g., 2'O-methyl ribosyl, 2'O-methoxyethyl ribosyl, 2'fluoro ribosyl, 2'amino ribosyl, and the like). An example of non-natural bases that are used in the art are isocytidine and isoguanine.

A label monomer as used herein is intended to mean an individual measurable moiety, such as a radioisotope, fluorochrome, dye, enzyme, nanoparticle, chemiluminescent marker, biotin, or other moiety known in the art that is measurable by analytical methods. A label monomer can be attached to a nucleotide using methods well known in the art and exemplified herein.

Radioisotopes are an example of label monomers that can be utilized by the invention. Several radioisotopes can be used as label monomers for labeling nucleotides including, for example, $^{32}P$, $^{33}P$, $^{35}S$, $^{3}H$, and $^{125}I$. These radioisotopes have different half-lives, types of decay, and levels of energy which can be tailored to match the needs of a particular experiment. For example, $^{3}H$ is a low energy emitter which results in low background levels, however this low energy also results in long time periods for autoradiography. Radioactively labeled ribonucleotides and deoxyribonucleotides are commercially available. Nucleotides are available that are radioactively labeled at the first, or α, phosphate group, or the third, or γ, phosphate group. For example, both [α-$^{32}P$]dATP and [γ-$^{32}P$]dATP are commercially available. In addition, different specific activities for radioactively labeled nucleotides are also available commercially and can be tailored for different experiments.

Another example of label monomers that can be utilized by the invention are fluorophores. Several fluorophores can be used as label monomers for labeling nucleotides including, for example, fluorescein, tetramethylrhodamine, and Texas Red. Several different fluorophores are known, and more continue to be produced, that span the entire spectrum. Also different formulations of the same fluorophore have been produced for different applications. For example, fluorescein, can be used in its isothiocynanate form (FITC), as mixed isomer or single isomer forms of carboxyfluorescein succinimidyl ester (FAM), or as isomeric dichlorotriazine forms of fluorescein (DTAF). These labels are chemically distinct, but all emit light with a peak between 515-520 nm. In addition to the chemical modifications of fluorescein, completely different fluorophores have been synthesized that have the same or very similar emission peaks as fluorescein. For example, the Oregon Green dye has virtually superimposable excitation and emission spectra compared to fluorescein. Other fluorophores such as Rhodol Green and Rhodamine Green are only slightly shifted in their emission peaks and so also serve functionally as substitutes for fluorescein. In addition, different formulations or related dyes have been developed around other fluorophores that emit light in other parts of the spectrum.

Amine-reactive and thiol-reactive fluorophores are available and used for labeling nucleotides and biomolecules. Generally, nucleotides are fluorescently labeled during chemical synthesis, for example, incorporation of amines or thiols during nucleotide synthesis permit addition of fluorophores. Fluorescently labeled nucleotides are commercially available. For example, uridine and deoxyuridine triphosphates are available that are conjugated to ten different fluorophores that cover the spectrum.

Fluorescent dyes that can be bound directly to nucleotides can also be utilized as label monomers. For example, FAM, JOE, TAMRA, and ROX are amine reactive fluorescent dyes that have been attached to nucleotides and are used in automated DNA sequencing. These fluorescently labeled nucleotides, for example, ROX-ddATP, ROX-ddCTP, ROX-ddGTP and ROX-ddUTP, are commercially available.

Non-radioactive and non-fluorescent label monomers are also available. For example, biotin can be attached directly to nucleotides and detected by specific and high affinity binding to avidin or streptavidin which has been chemically coupled to an enzyme catalyzing a colorimetric reaction (such as phosphatase, luciferase, or peroxidase). Digoxigenin labeled nucleotides can also similarly be used for non-isotopic detection of nucleic acids. Biotinylated and digoxigenin-labeled nucleotides are commercially available.

Very small particles, termed nanoparticles, also can be used as label monomers to label nucleic acids. These particles range from 1-1000 nm in size and include diverse chemical structures such as gold and silver particles and quantum dots.

When irradiated with angled incident white light, silver or gold nanoparticles ranging from 40-120 nm will scatter monochromatic light with high intensity. The wavelength of the scattered light is dependent on the size of the particle. Four to five different particles in close proximity will each scatter monochromatic light which when superimposed will give a specific, unique color. The particles are being manufactured by companies such as Genicon Sciences. Derivatized silver or gold particles can be attached to a broad array of molecular probe molecules including, proteins, antibodies, small molecules, receptor ligands, and nucleic acids. For example, the surface of the particle can be chemically derivitized to allow attachment to a nucleotide.

Another type of nanoparticle that can be used as a label monomer are quantum dots. Quantum dots are fluorescing crystals 1-5 nm in diameter that are excitable by a large range of wavelengths of light. These crystals emit light, such as monochromatic light, with a wavelength dependent on their chemical composition and size. Quantum dots such as CdSe, ZnSe, InP, or InAs possess unique optical properties. These particles have been used in the semi-conductor industry for several years, but are just now being applied to molecular biology applications.

Many dozens of classes of particles can be created according to the number of size classes of the quantum dot crystals. The size classes of the crystals are created either 1) by tight control of crystal formation parameters to create each desired size class of particle, or 2) by creation of batches of crystals under loosely controlled crystal formation parameters, followed by sorting according to desired size and/or emission wavelengths. Use of quantum dots for labeling particles, in the context of the present invention, is new, but is old in the art of semiconductors. Two examples of earlier references in which quantum dots are embedded within intrinsic silicon epitaxial layers of semiconductor light emitting/detecting devices are U.S. Pat. Nos. 5,293,050 and 5,354,707 to Chapple-Sokol, et al.

Due to their very small size the quantum dots can be coupled into oligonucleotides directly without affecting the solubility or use of the oligonucleotide. The invention requires that only one oligonucleotide molecule is coupled to each nanoparticle. To synthesize an oligonucleotide-nanoparticle complex in a 1:1 ratio by conventional batch chemistry, both the oligonucleotide and the nanoparticle require a single reactive group of different kinds that can be reacted with each other. For example, if an oligonucleotide has an amino group and a nanoparticle has an aldehyde group, these groups can react to form a Schiff base. An oligonucleotide can be derivitized to attach a single amino or other functional group using chemistry well known in the art. However, when a nanoparticle is derivatized, it is covered with a chemical reagent which results in coating the entire surface of the nanoparticle with several functional groups.

The invention provides a method of coupling one oligonucleotide to one nanoparticle by chemically coupling the oligonucleotide on a solid surface such as the glass support used for the oligonucleotide synthesis. For example, commercially available resins for oligonucleotide synthesis such as long chain alkylamino controlled pore glass (lcaa CPG) can be used. Alternatively, a flat surface such as a derivitized microscope slide can be used. The surface density of the nascent oligonucleotide chains should be lower than the diameter of the nanoparticle. This can be achieved by either choosing a glass support with low surface density of the reactive groups, or by using diluted reagent for the first step of the oligonucleotide synthesis so that the surface is not saturated. Another point of consideration when using the standard glass matrices for oligonucleotide synthesis is to use a pore diameter higher than the nanoparticle diameter to ensure the flow of the reagents. For example, an oligonucleotide can be synthesized on a diluted basis relative to the solid support, for example one tenth of a normal synthesis, to ensure good spacing of the oligonucleotides on the glass support. After the oligonucleotide is synthesized with a reactive functional group, for example, an amino group, derivitized nanoparticles are passed over the glass support to react with the oligonucleotides. A sufficiently large pore size of the glass support can be chosen to prevent clogging with nanoparticles. For example, a pore size of about 200 nm can be used. After the reaction is complete, un-reacted groups on the nanoparticle can be blocked and the complexes can be uncoupled from the glass support.

The labels of the invention are bound to nucleic acids through nucleotides in the nucleic acid. A nucleotide can be attached to a label monomer first and then the label monomer:nucleotide can be incorporated into a nucleic acid, or an existing nucleic acid can be labeled by attaching a label monomer to a nucleotide within the nucleic acid.

A label monomer can be attached to a nucleotide using a variety of methods well known in the art and described herein. For example, the label monomer can be directly attached to the nucleotide in a 1:1 correspondence by incorporation of a radioactive phosphate into the phosphate backbone of the nucleotide. Also, for example, a general method for labeling phosphates with a fluorescent label that employs an imidazole derivative prepared from a BODIPY FL hydrazide has been reported (Wang and Giese, Anal. Chem. 65: 3518 (1993).

Depending on the labeling moiety used, it can be desirable to derivitize or chemically modify a nucleotide in order to bind the label monomer. These methods and chemistries are known in the art. In addition, a linker can be used to attach a label monomer to a nucleotide in a 1:1 correspondence. For example, a fluorescently labeled nucleotide such as fluorescein-12-dUTP can have a fluorophore monomer attached via a four-atom aminoalkynyl group to the dUTP molecule.

These nucleotides attached to label monomers can be incorporated into a nucleic acid using several methods for labeling nucleic acids well known in the art. For example, enzymes such as DNA or RNA polymerases, Taq polymerases, terminal deoxynucleotidyl transferases, or reverse transcriptases can be used to incorporate labeled nucleotides into nucleic acids.

Labeled nucleotides can be incorporated into nucleic acids, for example, by nick translation. In this procedure DNAse I is used to create single-strand nicks in double stranded DNA and then the 5' to 3' exonuclease and 5' to 3' polymerase actions of E. coli DNA polymerase I are used to remove stretches of single stranded DNA starting at the nicks and replace them with new strands made by incorporation of labeled nucleotides. Nick translation can utilize any labeled nucleotide including radioactively labeled nucleotides and biotinylated or digoxigenin labeled nucleotides. In a similar way T4 DNA polymerase can be used to incorporate labeled nucleotides. In addition, labeled nucleotides can be incorporated into nucleic acids using the polymerase chain reaction (PCR) and Taq polymerases. The degree of labeling can be controlled by including one, or up to all four labeled nucleotides. In addition, the degree of labeling can be controlled by increasing or decreasing the concentration of the labeled nucleotide(s).

Other methods for labeling nucleic acids include generating single-stranded cDNA from RNA by using a reverse transcriptase in the presence of labeled nucleotides. In addition, DNA can be cloned into a vector with SP6 or T7 polymerase sites. Transcription in the presence of SP6 or T7 RNA polymerase and labeled nucleotides results in a labeled RNA transcript. The transcript can be labeled to different degrees by including one or more labeled nucleotides. In addition, several nucleotides within a nucleic acid can be labeled, for example, by cloning DNA into a bacteriophage M13 based vector. Then the Klenow fragment of DNA polymerase I and the M13 universal probe primer can be used to synthesize the complementary stand with incorporation of labeled nucleotides.

Several methods are described above for incorporation of labeled nucleotides into newly synthesized nucleic acids. Existing nucleic acids can also be labeled using several methods known in the art. For example, RNA or DNA can be end-labeled with [.gamma.-.sup.32P]ATP and T4 polynucleotide kinase. This kinase can be used to transfer the radioactive phosphate of ATP to a free 5' OH group in either DNA or RNA. The enzyme also has a phosphatase activity and so two reactions are possible. In the forward reaction, the enzyme catalyzes phosphorylation following removal of 5' terminal phosphates with alkaline phosphatase (or other phosphatase). In the exchange reaction, the kinase catalyzes the exchange of an existing 5' phosphate with the third or .gamma. phosphate of ATP. The latter reaction is carried out in the presence of excess ATP and ADP for efficient phosphorylation. Using this method the radioactive phosphate of ATP is transferred to the end of the nucleic acid molecule.

Nucleic acids can also be labeled with terminal deoxynucleotidyl transferase which adds labeled nucleotides onto the 3' end of DNA fragments. Both single and double-stranded DNAs are substrates for this enzyme. The large (Klenow) fragment of E. coli DNA polymerase I can also be used to label the ends of nucleic acids. Since this enzyme has a 5' to 3' polymerase activity it can be use to "fill in" the 3' ends of DNA fragments opposite of 5' extensions or overhangs with labeled nucleotides. End-labeling of nucleic acids using polynucleotide kinase or terminal deoxynucleotidyl transferase results in the incorporation of one label per nucleic acid. The "fill in" reaction can be used to label the nucleic acid at one nucleotide per nucleic acid or at more than one nucleotide per nucleic acid.

In addition, nucleic acids can be labeled by modification of nucleotides within the nucleic acid. For example, cytidine residues in DNA and RNA can be modified by reaction with sodium bisulfite to form sulfonate intermediates that can then be directly coupled to hydrazides or aliphatic amines. Virtually any of the fluorescent, biotin or other hydrazides or aliphatic amines can be used in this reaction. The bisulfite-activated cytidylic acid can also be coupled to aliphatic diamines such as ethylenediamine. The amine-modified DNA or RNA can then be modified with any of the amine-reactive dyes. In addition, phosphate groups can be targeted in nucleic acids for labeling. Although phosphate groups of nucleotides are not very reactive in aqueous solution, their terminal phosphate groups can react with carbodiimides and similar reagents in combination with nucleophiles to yield labeled phosphodiesters, phosphoramidates and phosphorothioates. For example, DNA can be reacted quantitatively with carbonyl diimidazole and a diamine such as ethylenediamine to yield a phosphoramidate that has a free primary amine and that this amine can then be modified with amino-reactive reagents. Fluorescent or biotinylated amines have been coupled to the 5' phosphate of tRNA using dithiodipyridine and triphenylphosphine.

The bond between labels and nucleic acids can be covalent bonds or non-covalent bonds that are stable to hybridization and washing conditions. The labels can be bound to a nucleic acid in a sequence specific manner, for example by the incorporation of a labeled nucleotide into DNA that has been digested by a restriction enzyme. Alternatively the labels can be bound to a nucleic acid in a non-sequence specific manner, for example by the incorporation of a label onto the terminal phosphate of a nucleic acid using [γ-$^{32}$P] ATP and T4 polynucleotide kinase.

Several types of nucleic acids can be utilized with this invention including a single- or double-stranded DNA or RNA molecule which can include, for example, genomic DNA, cDNA and mRNA. Nucleic acid molecules of both synthetic and natural origin can be used. A nucleic acid molecule of the invention can be of linear, circular or branched configuration, and can represent either the sense or antisense strand, or both, of a native nucleic acid molecule. Nucleotide bases not found in nature such as isocytidine and isoguanine can be incorporated into the nucleic acid.

Labels can bind to nucleic acids in a number of diverse ways. For example, a particular label monomer can be bound to a nucleic acid at only one position in the nucleic acid or at many positions in the nucleic acid. In addition, a particular label monomer can be bound to a nucleic acid and one or more other label monomers can also bound to the same nucleic acid. In this case the label can contain a mixture of two or more different labels. Furthermore, nucleic acids labeled with any or all of these combinations can be bound to another nucleic acid through hybridization.

Additional diversity is introduced when the nucleic acid is branched. One example of a branched nucleic acid is a dendrimer. Dendrimers are composed of layers of nucleic acid, each layer being composed of partially single-stranded heteroduplexes yielding a three-dimensional structure composed of nucleic acid. Various configurations of nucleic acid molecules can give rise to a large number of differently shaped dendritic structures including, for example, a dendrimer with 1 stem and 81 branches, or dendrimers with fork-like, comb-like or bubbled structures. The outermost layer of a given dendrimer can have multiple single-stranded arms capable of hybridization with a complementary nucleic acid sequence. Due to the relatively large size of nucleic acid molecules, nucleic acid dendrimers can contain numerous labels with limited steric hindrance. Use of dendrimers can multiply the signal generated by a labeled nucleic acid by a pre-determined factor equal to the number of branches.

Several unique combinations of labels can be formed using branched nucleic acids. For example, by using different chemical protective groups, one label monomer can bind to one branch while one or more other label monomers bind to other branches. Furthermore, labeled nucleic acids can be attached in various combinations to the branches of a dendrimer through hybridization.

The invention provides a diverse population of 30, or about 40, 60, 80, 100, 120, 140, or 150 unique labels bound to a nucleic acid. Part of this population can be made up of different individual label monomers. The invention also provides unique labels made from a combination of two or more different labels. This can increase the number of unique labels substantially.

A unique label is a label that generates a signal that is distinguishable from other labels in the same mixture. Therefore, designation as a unique label is dependent upon the sensitivity of the detection equipment that is used. For example, where fluorescent or nanoparticle labels are used a CCD camera can be used to detect the labels. The sensitivity of this equipment depends on the manufacturer, model, and design of the equipment. In addition, several parameters can be set by the user in order to achieve maximum sensitivity. For example, the use of different filter sets can increase the sensitivity of detection for certain experiments.

The ability to distinguish different labels also depends on the particular properties of the label. For example, some fluorophores emit light within a broad peak or range of wavelengths while other fluorophores emit light within a narrow peak. Fluorophores that emit light within a broad peak can obscure neighboring peaks. In addition, the shapes of the emission peaks from different fluorophores varies. For example, some fluorophores have a peak that has a sharp ascent, but a broad trailing end that can obscure neighboring peaks. If two peaks cannot be distinguished then the two labels associated with those peaks cannot be considered unique. Where fluorescent labels are used, the labels would emit fluorescent light at distinct, essentially non-overlapping wavelengths distant from each other by at least 1 nm, 5 nm, 10 nm, 15 nm, 20 nm, 25 nm, and preferably 30 nm, 35 nm, 40 nm, 45 nm, and more preferably by at least 50 nm. For example, the emission peak of dye #1 could be 585 nm, and the peak emission of dye #2 could be 630 nm.

A unique label is a label that generates a signal that is distinguishable from other labels in the same mixture. A unique label, therefore, is dependent on the other labels that are included in the mixture. For example, fluorescein which has an emission spectra peak at 518 nm and rhodamine red with an emission spectra peak of 590 nm have clearly distinct emission peaks and hence both are considered to be unique labels when included together in a mixture. However, if another fluorophore is added that has an emission peak that overlaps with fluorescein or rhodamine red, these labels would not be unique. For example, if Oregon green (emission spectra peak 522 nm) is added to the above mixture the emission peak of fluorescein and Oregon Green can overlap so much that, depending on the detection equipment used, they cannot be clearly distinguished from each other and hence neither fluorescein nor Oregon Green can act as unique labels in that particular mixture.

Often several formulations of the same label or related labels are synthesized for use in different applications, and while these labels have different chemical properties, they are not distinct in terms of detection. For example, fluorescein, can be used in its isothiocynanate form (FITC), as mixed isomer or single isomer forms of carboxyfluorescein succinimidyl ester (FAM), or isomeric dichlorotriazine forms of fluorescein (DTAF). These labels are chemically distinct, but all emit light with a peak between 515-520 nm and hence would overlap so as to appear identical on most currently available detection equipment. In addition to the chemical modifications of fluorescein, completely different fluorophores have been synthesized that have the same or very similar emission peaks as fluorescein. For example, the Oregon Green dye has virtually superimposable excitation and emission spectra compared to fluorescein. Other fluorophores such as Rhodol Green and Rhodamine Green are only slightly shifted in their emission peaks and so also serve functionally as substitutes for fluorescein.

A limited number of different label monomers are known that can be used together in a mixture and still provide unique signals. For example, five analytes can be distinctly labeled using the BODIPY fluorophore set from Molecular Probes (Eugene, Oreg.). These fluorophores have the following distinct emission peaks: BODIPY FL(513), BODIPY R6G (550), BODIPY TMR (574), BODIPY 581/591 (592) and BODIPY TR (617). In order to obtain clear results using currently available detection equipment, the number of different fluorophores that can be used is less than thirty.

Unique labels of the invention also can be generated by combining two or more different label monomers to make a new label. The signal from the resulting label must be distinguishable from the signals of other labels used in the same experiment in order to be a unique label. For example, a nucleic acid labeled with both fluorescein and rhodamine will emit light at a different wavelength than a nucleic acid labeled with either fluorescein or rhodamine alone.

In this invention, various ratios of different label monomers bound to nucleic acids can be combined to generate a diverse population of unique labels that can include up to $10^{17}$ or more unique labels. For example, a nucleic acid labeled with two fluorescein labeled nucleotides and three rhodamine labeled nucleotides will emit light at a different wavelength compared to a nucleic acid labeled with three fluorescein nucleotides and two rhodamine nucleotides. In another example, a nucleic acid could be labeled with different ratios of three or more label monomer:nucleotides which greatly increases the variety of unique labels that can be generated.

The signal generated by each of the label monomers bound to the nucleotides can be normalized to have about the same unit signal. For example, if fluorescent monomer A is known to emit a different quanta of light as fluorescent monomer B, the signal from unique labels that contain a pre-determined number of these monomers can be normalized based on the known signal properties of the label monomers and the number of each monomer present in the unique label. Different numbers of labels can be used in the invention and so different multiples of the same unit signal can be utilized by the invention. For example, a nucleic acid can be labeled with two fluorophores and another nucleic acid can be labeled with six fluorophores. The second nucleic acid will have three times the signal of the first nucleic acid. Since the number of label monomers attached to each nucleic acid is known, the signals from the labeled nucleic acids can be normalized based on the number of label monomers present. For example, the signal from the nucleic acid with six fluorophores can be divided by three which normalized the signal relative to the signal from the nucleic acid with two fluorophores.

This method of producing labels results in important advantages over existing techniques such as microarray formats. Since each analyte is uniquely identified by a label with about the same unit signal, it allows the labels to be directly counted resulting in a digital read-out of each molecular species in a mixture. In contrast, microarray data must undergo several intermediate transformations to quantitate the number of molecules which results in a less precise analog output. In addition, using a diversity of labels with the same unit signal allows the detection method to operate in a narrow dynamic range resulting in improved sensitivity of the system since the trade-off between sensitivity and dynamic range is avoided.

The invention provides a diverse population of uniquely labeled probes. This population of probes contains about 30 or more target specific nucleic acid probes each attached to a unique label bound to a nucleic acid. In addition, the invention provides a diverse population of uniquely labeled probes containing a diversity of 50, 100, 200, 500, 1,000, 2,000, 5,000, $1\times10^4$, $3\times10^4$ and about $1\times10^5$ or more different labels. As described above, these unique labels can contain a mixture of two or more different labels and comprise about the same unit signal or multiple thereof.

The invention provides a diverse population of uniquely labeled probes in which a target specific nucleic acid contains a nucleic acid bound to a unique label. In addition, the invention provides a diverse population of uniquely labeled probes containing two attached populations of nucleic acids, one population of nucleic acids containing thirty or more target specific nucleic acid probes, and a second population of nucleic acids containing a nucleic acid bound by a unique label.

A target specific probe is intended to mean an agent that binds to the target analyte selectively. This agent will bind with preferential affinity toward the target while showing little to no detectable cross-reactivity toward other molecules.

The target analyte can be any type of macromolecule, including a nucleic acid, a protein or even a small molecule drug. For example, a target can be a nucleic acid that is recognized and bound specifically by a complementary nucleic acid including for example, an oligonucleotide or a PCR product, or a non-natural nucleic acid such as a locked nucleic acid (LNA) or a peptide nucleic acid (PNA). In addition, a target can be a peptide that is bound by a nucleic acid. For example, a DNA binding domain of a transcription factor can bind specifically to a particular nucleic acid sequence. Another example of a peptide that can be bound by a nucleic acid is a peptide that can be bound by an aptamer. Aptamers are nucleic acid sequences that have three dimensional structures capable of binding small molecular targets including metal ions, organic dyes, drugs, amino acids, co-factors, aminoglycosides, antibiotics, nucleotide base analogs, nucleotides and peptides (Jayasena, S. D., *Clinical Chemistry* 45:9, 1628-1650, (1999)) incorporated herein by reference. Further, a target can be a peptide that is bound by another peptide or an antibody or antibody fragment. The binding peptide or antibody can be linked to a nucleic acid, for example, by the use of known chemistries including chemical and UV cross-linking agents. In addition, a peptide can be linked to a nucleic acid through the use of an aptamer that specifically binds the peptide. Other nucleic acids can be directly attached to the aptamer or attached through the use of hybridization. A target molecule can even be a small molecule that can be bound by an aptamer or a peptide ligand binding domain.

The invention provides a method of producing a population of labels consisting of synthesizing a population of nucleic acids bound to a predetermined ratio of at least two different labels. The method involves incorporating labeled nucleotides into a repeated nucleic acid structure using a DNA polymerase. The repeated nucleic acid structures can be designed to allow incorporation of a pre-determined ratio of labels. Using this method several unique labels can be generated from a small number of starting labels.

A specific example of this method where ten unique labels are made from two different labels is provided in Example 1. Briefly, ten unique templates of a 220 base pair single-stranded DNA are synthesized. The templates consist of a pre-determined ratio of the following 20 base pair repeats where n+m=11:

(SEQ ID NO: 1) 5' (ACTCTCTCTCTCTCTCTC)n (GCTCTCTCTCTCTCTCTC)m 3' (SEQ ID NO: 2). The second strand is synthesized using the primer GAGAGAGAGA (SEQ ID NO: 3), Klenow polymerase, DNA ligase, dGTP, DATP, and dCTP and dUTP each labeled with a different fluorophore. The labeled nucleotides will be incorporated into the DNA in a unique ratio determined by the ratio of the two repeats. In this example, the end result is ten uniquely labeled nucleic acids where the set ratio of the two fluorophores is 1:10, 2:9, 3:8, 4:7, 5:6, 6:5, 7:4, 8:3, 9:2, and 10:1.

In Example 1, two different labels resulted in ten unique labels. Using the same protocol, three different labels would result in 30 unique labels, four different labels would result in 60 unique labels, five different labels would result in 100 unique labels, and so on. Several variations of the method will be apparent to one skilled in the art. For example, the number of repeats can be changed to be less than or greater than ten. An increased number of repeats will increase the number of unique ratios possible. This will result in an increase in the number of unique labels that can be generated from the same number of starting different labels. Also in Example 1, the ratio between the two fluorophores can include 0:11 and 11:0 which results in two additional labels that contain one fluorophore or the other.

One skilled in the art will recognize that the sequence of the templates can differ from that shown above. For example, the repeat sequence in the template can be $(GA)_n$ instead of $(CT)_n$. In addition, the repeat sequence could be a single nucleotide homopolymer such as $(A)_n$. With a homopolymer template, three labeled nucleotides can be incorporated in different ratios thus increasing the number of unique labels that can be generated. It is possible using the claimed method to generate a large number of unique labels including 40, 60, 80, 100, 120, 140, 150, 200, 500, 2,000, 5,000, $1\times10^4$, $3\times10^4$, $1\times10^5$ or more labels. Again as described above, these unique labels can comprise about the same unit signal or multiple thereof.

Another possible modifications of the method is to change the length of the repeat, for example, to less than or greater than 20 base pairs. The repeat serves to separate the labeled nucleotides and therefore to decrease possible interference between the labels. In the case of a fluorescent label, this can decrease quenching between fluorophores. In addition, the protocol for incorporating the labeled nucleotides into the DNA can be modified as would be clear to one skilled in the art and as described herein.

In one embodiment, the labeled DNA described above can be attached to a dendrimer. Oligonucleotide tags can be synthesized at the branches of the dendrimer to allow binding of the labeled DNA. For example, a linker can be attached to the labeled DNA described above that corresponds to an oligonucleotide tag on the branches of the dendrimer. Several types of linkers are known to one skilled in the art. For example, a restriction enzyme linker can be attached to the labeled DNA. These linkers are double-stranded oligonucleotides that contain the recognition sequence of a particular restriction enzyme. These linkers can be ligated onto double-stranded DNA using a DNA ligase and digested using the appropriate restriction enzyme. The result is an overhanging single stranded sequence that is available to hybridize to another nucleic acid.

The labeled DNA described above can be directly attached to a target specific probe. In addition, the labeled DNA can be indirectly attached to a target specific probe, for example, through use of a bridging nucleic acid. One or more of these labels can be attached to each target specific probe. Binding of a uniquely labeled target specific probe to a target analyte results in the unique tagging of that analyte. This tagging allows identification of the target analyte from a mixture of analytes.

The number of unique labels can be further increased by combining the unique labels described above in different combinations. The invention provides a method of attaching a label to a nucleic acid probe, comprising hybridizing a nucleic acid probe having a genedigit to an anti-genedigit having a label. The anti-genedigits that contain the labels described above are hybridized to genedigits. Genedigits can be linked together in unique combinations creating an even larger number of unique labels. The modular design of the genedigits allows for flexibility in the number of unique labels that are generated. For example, if a large number of genedigit modules are used, a large number of unique templates will be available for attachment of unique labels. The number of templates generated can be adjusted to cover the number of species in the mixture.

A genedigit can be a region of pre-determined nucleotide or amino acid sequence that serves as an attachment point for a label. The genedigit can have any sequence including, for example, a single unique sequence or a sequence containing repeated core elements. However, each genedigit has a unique sequence which differentiates it from other genedigits. When added to a complex mixture of targets, a nucleic acid genedigit can contain non-natural bases such as isocytidine and isoguanine which can reduce hybridization to naturally occurring target sequences. The sequence, length of a core element, and number of repeated core elements can be varied according to the particular requirements of an experiment and will be clear to one skilled in the art. For example, a nucleic acid core element can be between about 5 and 12 base pairs in length and the core element can be repeated once to about ten times.

Different genedigits can be synthesized that have a core unit that differs from the core units of other genedigits, for example, by at least two bases. By combining these unique genedigits in various combinations, a highly diverse number of structures can be synthesized. For example, 50 genedigits with unique sequences can be synthesized and split into five groups containing ten genedigits in each group. The genedigits of each group can be synthesized to have a short tag on each end. One genedigit from each group is then linked together using an adapter oligonucleotide that is complimentary to the tags that are common for each group. In this example, $1\times10^5$ ($10\times10\times10\times10\times10$) unique combinations are possible.

Genedigits serve as attachment points for the unique labels described above. Since genedigits can be linked together in unique combinations this greatly increases the number of unique labels. By linking together genedigits, a large number of unique labels can be generated including 200, 500, 2,000, 5,000, $1\times10^4$, $3\times10^4$, $1\times10^5$ or more unique labels.

The invention provides a method of attaching a label to a nucleic acid probe, comprising hybridizing a nucleic acid probe having a genedigit to an anti-genedigit having a label where the genedigit comprises a set of three or more repeat sequences, and the anti-genedigit comprises a cognate set of at least two complimentary repeat sequences where the anti-genedigit specifically hybridizes to the genedigit through a sequence having a complexity less than the number of hybridized base pairs.

An example of a nucleic acid genedigit is given in Example 2. Briefly, in this example an eight base pair core element containing the non-natural bases isocytidine and isoguanine is repeated five times. This results in a 40 base pair genedigit. In this example the anti-genedigit consists of a sequence that is complimentary to three of the five core elements in the genedigit. An anti-genedigit can contain the same number, or a lesser number, of repeat sequences compared to the genedigit as long as the anti-genedigit is able to specifically bind to the genedigit. In this example, the anti-genedigit is a 24 base pair sequence that can bind to the 40 base pair genedigit in three different registers (see FIG. 1C).

The anti-genedigit in this specific example is a 24 base pair sequence that only has the complexity of an eight base pair sequence. Complexity refers to the degree of repeated elements between two nucleic acids that are being hybridized together in a solution. When the nucleic acid molecules that are to be hybridized contain repeated core elements or homopolymeric regions, there are many possible pairing opportunities and so the hybridization proceeds quickly. When the nucleic acid molecules that are to be hybridized do not contain any repeated core elements then there is only one way that the two sequences can be hybridized and so the hybridization proceeds more slowly. Sequences that hybridize quickly are said to have a low complexity, while sequences that take longer to hybridize have a higher complexity. In this example, a 40 base pair genedigit sequence made up of five direct repeats of an 8 base pair core element, can be hybridized to a 24 base pair anti-genedigit containing three repeats of the 8 base pair core repeat in three different registers. Thus the anti-genedigit can hybridize to the 40 base pair genedigit through a 24 base pair sequence that only has a complexity of an 8 base pair sequence. The advantage of this method is that hybridization will proceed more quickly and efficiently.

In the specific example above, an 8 base pair core element was describe; however, a core element can be more or less than 8 base pairs. For example, a core element can be between 5 and 12 base pairs. A change in the core element of a repeat will correspondingly change complexity. For example, if a core element is between 5 and 12 base pairs, complexity will be between 5 and 12. In addition, an anti-genedigit can bind to a genedigit using all or part of its sequence. In the example above, a 24 base pair anti-genedigit can bind to the genedigit with less than 24 bases, for example, 15 to 23 base pairs.

The anti-genedigit serves as a connector between the genedigit and the label. The genedigit is bound by the anti-genedigit and the anti-genedigit is bound to a label directly or indirectly by being bound to a dendrimer that has a label(s) attached. The anti-genedigit also contains a linker sequence that allows attachment to a dendrimer. For example, an oligonucleotide tag can be synthesized at the stem of a dendrimer that is complementary to the linker sequence on the anti-genedigit. As described above, several types of linkers can be used. In this way the repeat sequences of the anti-genedigit are free to hybridize with their corresponding genedigit resulting in the specific attachment of a label to a genedigit.

Genedigits and anti-genedigits can be comprised of nucleic acids, including aptamers, as well as macromolecules other than nucleic acids. For example, a genedigit can be comprised of an amino acid sequence that is bound by an anti-genedigit that is a nucleic acid that binds specifically to the amino acid sequence in the genedigit, or the anti-genedigit can be an amino acid sequence, including an antibody or antibody fragment, that specifically binds to the amino acid sequence in the genedigit.

The invention provides for a method whereby a target specific probe can be attached to one or more genedigits to form a "specifier." The genedigits can be directly linked or can be attached to the target specific region using an intervening or adapting sequence. As described above, the target specific area can be a nucleic acid, including an aptamer, or the target specific area can be an amino acid sequence, including an antibody or antibody fragment. The target specific area is designed to specifically bind an analyte in a mixture. In this way an analyte can be labeled with a unique label.

A specifier can contain one to several genedigits. For example, a specifier can contain four or five or more gendigits. The number of genedigits in a specifier will determine the number of unique labels that are available to bind to analytes in a mixture. Therefore, in order to label each analyte in a complex mixture, a large population of specifiers can be synthesized that contain several combinations of genedigits. Alternatively, to label one or a small number of analytes in mixture, a specifier or specifiers can be synthesized that contain one or a few genedigits. In addition, a specifier can contain a common tag such as a biotin tag. These tags can facilitate synthesis and purification of specifiers.

The invention additionally provides a method of producing a population of target specific nucleic acid probes. The method consists of producing a first population of two or more target specific probes each having at least one genedigit, where the genedigit contains a set of three or more repeated sequences then producing a second population of nucleic acids having an anti-genedigit with at least two complimentary repeated sequences, and finally hybridizing the first and second populations of nucleic acids to produce a population of target specific probes attached to an anti-genedigit where the anti-genedigit hybridizes to the genedigit through a sequence having a complexity less than the number of hybridized base pairs.

The invention also provides a method for producing a population of uniquely labeled nucleic acid probes. The method consists of synthesizing a population of target specific nucleic acid probes each having a different specifier; then synthesizing a corresponding population of anti-genedigits each having a unique label, and finally hybridizing the populations of target nucleic acid probes to the anti-genedigits, to produce a population where each of the target specific probes is uniquely labeled.

The invention further provides a method for detecting a nucleic acid analyte, by contacting a mixture of nucleic acid analytes with a population of target specific probes each attached to a unique label under conditions sufficient for hybridization of the probes to the target and measuring the resulting signal from one or more of the target specific probes hybridized to an analyte where the signal uniquely identifies the analyte.

The nucleic acid analyte can contain any type of nucleic acid, including for example, an RNA population or a population of cDNA copies. The invention provides for at least one target specific probe for each analyte in a mixture. The invention also provides for a target specific probe that contains a nucleic acid bound to a unique label. Furthermore, the invention provides two attached populations of nucleic acids, one population of nucleic acids containing a plurality of target specific nucleic acid probes, and a second population of nucleic acids containing a nucleic acid bound by a unique label. When the target specific probes are attached to unique labels, this allows for the unique identification of the target analytes.

The methods of the invention are advantageous because hybridizations can be performed in solution in a small volume (0.01-2.0 µl) which ensures high concentration of the nucleic acids which will drive the hybridization rate. Two different types of hybridizations are utilized by the methods of invention. The first hybridization is between a complex mixture of analytes and the specifiers and the second type of hybridization is between the specifiers and the labels.

In the first type of hybridization between a complex mixture of analytes and a population of specifiers, the specifiers are in excess. For example, the specifiers can be in 10 to about 100 fold excess over the analytes in the complex mixture. The kinetics of this reaction can be described by the following equation:

$$t_{1/2} = \frac{N \ln 2}{3.5 \times 10^5 \times L^{0.5} \times C_0}$$

where N is the complexity of the probe (the specifiers), L is the length, $C_0$ is the concentration of the probe, and $t_{1/2}$ is the time required for 50% completion of the reaction. Using this equation it is clear that higher concentrations of probe will result in shorter time required for 50% completion of the reaction. The sample in this hybridization can be either RNA or DNA. If the sample is not poly A RNA then it must first be tagged by some method, for example, platinum-digoxygenin. After the hybridization is complete, the duplexes containing the analyte and specifier are separated using the poly A, or the digoxygenin tag as a handle and washed from the excess specifier. The washed material is then used for the second hybridization.

In the second hybridization the isolated specifiers are mixed with labels. The labels are in excess over the specifiers and the kinetics follow the same kinetics as shown above for the first hybridization, and it is performed at an even faster rate because the complexity, N, is very low. The hybridized complexes containing specifiers and labels can be isolated using a biotin tag on the specifiers as a handle and processed further for detection.

The formation of macromolecule hybrids is dependent on several conditions known in the art, including temperature, salt concentration, and pH. Different conditions for the formation of nucleic acid hybrids are well known in the art and can be found in, for example, Hames and Higgins, Nucleic Acid Hybridisation: A Practical Approach, IRL Press, Oxford (1991). In addition, conditions for nucleic acid-protein and protein-protein interactions are well known in the art and can be found in, for example, Current Protocols in Molecular Biology (ed. Ausubel et al., Greene Publ., New York 1989) which is incorporated herein by reference.

The "specifier-label" complexes can be separated from one another, for example, by spreading them on a two-dimensional surface such as glass, or by splitting them in liquid droplets in a flow cytometer. In this example, visualization can be achieved either by scanning the 2-D surface or by flow cytometry. Co-localization of specific labels will determine the identity of the particular specifier, which will determine the identity of the particular analyte that the specifier bound initially.

The "specifier-label" complexes can be detected by various devices including but not limited to visual inspection, digital cameras, video cameras, photographic film, or the use of current instruments such as laser scanning devices, fluorometers, luminometers, photodiodes, quantum counters, plate readers, epifluorescence microscopes, scanning microscopes, confocal microscopes, or by other means for amplifying the signal such as a photomultiplier tube or other light detector capable of detecting the presence, location, intensity, excitation and emission spectra, fluorescence polarization, fluorescence lifetime and other physical properties of the fluorescent signal. Non-fluorescent signals can be detected using a Geiger counter, scintillation counters, chemiluminescence, enzyme assays, and autoradiography.

An example of a detection method that can be utilized by the invention is a CCD (charge-coupled device) camera. Use of this device requires that the specifier-label complexes are first spread on a glass slide. Since all complexes will have approximately the same total intensity this simplifies detection, because the camera can be adjusted for maximum sensitivity (maximum gain) and minimum dynamic range.

For example, if fluorescent dendrimers are used for labeling the sample can be excited at the corresponding absorption maxima and scanned at the corresponding emission maxima for each of the, for example, 8-10 fluorofors used. A benefit of CCD cameras is that they have very wide range of detection which allows for a choice of fluorofors with distant emission peaks. Thinned layer CCD cameras can detect from the soft X-ray to the near infrared spectrum.

Alternatively if nanoparticles labels are used the sample can be illuminated by angled white light and detection occurs at a few wavelengths. The number of wavelengths will depend on the quality of the camera used and its sensitivity and linearity. Cameras of good quality can reproducible distinguish millions of colors with only the three standard filters (red, green, and blue).

In the case of unique labels that contain more than one label monomer, the overall signal generated by the unique label can be determined. For example, an overall signal for a unique label containing several fluorophores can be determined using a spectrometer. In addition to detecting an overall signal generated from the unique label, the invention provides for the determination of the spatial location of starting labels (which can be label monomers or combinations of label monomers) within a unique label. For example, the labels within a unique label can be separated from one another using a flow-stretch technique (Henegariu et al., Biotechniques 31:246-250 (2001)) a receding meniscus technique (Yokota et al., Nuc. Acids Res. 25:1064-1070 (1997)) or an electrostretching technique (Matsuura et al., Nuc. Acids Res. 29:E79 (2001)).

The use of flow-stretching, receding meniscus, or electro-stretching techniques allows for the separation of the labels within a unique label so that one can determine spatially where a particular label is positioned in the unique label (Example V, VI, VII and VIII). Therefore, unique labels that have the same combination of starting labels and the same overall signal can be differentiated from one another based on the location of those labels within the unique label. This ability to locate the position of a label within a unique label allows for the position of the starting label to be used as a distinguishing characteristic when generating a set of unique labels. Hence, a complex set of unique labels can be generated using the same combination of starting labels by varying the position of the labels within a unique label.

An observed signal can be modified using methods known in the art. For example, an observed signal can include subtraction of non-specific noise. An observed signal can also include, for example, treatment of the measured quantity by routine data analysis and statistical procedures which allow meaningful comparison and analysis of the observed values. Such procedures include, for example, normalization for direct comparison of values having different scales, and filtering for removal of aberrant or artifactual values.

In the first type of hybridization described above between a complex mixture of analytes and a population of specifiers, the specifiers were in excess. In contrast, hybridization on standard microarrays occurs under conditions where the analyte is in excess compared to the labeled probe. In addition, on microarrays only a small fraction of this probe will actually hybridize to the cognate target during the course of the hybridization, and so target coverage at the end of the experiment is usually less than 5%. The target coverage using the methods of the invention are theoretically 100% because the label is in excess compared to the target analyte.

One of the advantages of 100% target coverage is that this allows the target analytes to be directly counted since each analyte is bound by a label. Using the methods of the invention, molecular species can be directly counted one by one. Direct counting, or a digital output, is preferable to the indirect quantitation methods used for microarrays because the data does not need to go through several intermediary transformations. If the detection equipment directly counts the number of particles emitted it is said to have a digital output, however if the direct counts undergo several intermediary transformations then the data has an analog output. Quantitation data from microarrays is known to be subject to several distortions due to data extrapolation.

Another consequence of low target coverage in microarrays is that highly sensitive equipment is needed to detect the low amount of signal. However, since microarrays require a high dynamic range for signal detection, sensitivity is decreased because of the trade-off between sensitivity and dynamic range. The methods of the invention use a limited number of labels to create a large number of unique label combinations. This allows the detection method to operate in a narrow dynamic range. In contrast, microarray methods require a large dynamic range (4 orders of magnitude or more) to account for the large differences in abundance of the different molecular species. The low requirements in terms of dynamic range required by the methods of the invention will improve the sensitivity of the system since the trade-off between sensitivity and dynamic range is avoided.

The invention further provides a method of detecting a nucleic acid analyte. The method entails contacting a mixture of nucleic acid analytes under conditions sufficient for hybridization with a target specific probe having at least one genedigit where the genedigit has a set of three or more repeated sequences, then contacting that mixture with an anti-genedigit having a cognate set of at least two complimentary repeated sequences, and finally detecting a hybridized complex containing the analyte, target specific probe and anti-genedigit where the anti-genedigit hybridizes to the genedigit through a sequence having a complexity less than the number of hybridized base pairs.

The invention also provides a method of detecting a nucleic acid analyte as above where the anti-genedigit(s) each have a unique label.

The methods of the invention provide for detection of analytes in mixtures. The mixture can contain several types of analytes or the mixture can contain just one type of analyte. In addition, the mixture could contain just a single copy of an analyte. If the target analyte has an unknown sequence or structure, a large population of target specific specifiers can be added to the mixture. This population can include specifiers with target specific regions of pre-determined sequence or structure or specifiers can be used with target specific regions of random sequence or structure. Alternatively, if the target analyte has a known sequence or structure, a particular specifier containing a region that will specifically bind to that sequence or structure can be used either alone or in combination with other specifiers.

The methods of the invention are suited to nucleic acid analytes as well as analytes with other structures. A population of specifiers can be generated for any analyte where a target specific region can be found that specifically interacts with that analyte. For example, a protein analyte could be bound specifically by a nucleic acid or a peptide or an antibody, all of which can be linked to nucleic acid genedigits. The target specific region can also be attached to amino acid containing genedigits. In addition, the ability of nucleic acid aptamers to bind a wide variety of analytes allows these structures to be used in the target specific regions of specifiers. Several combinations are possible as long as the specifiers specifically bind to the analytes.

The invention further provides a nucleic acid labeling kit, containing a set of genedigits, a set of anti-genedigits and a unique set of labels bound to a nucleic acid. The kit can include other reagents as well, for example, buffers for performing hybridization reactions, linkers, restriction endonucleases, and DNA ligases. The kit also will include instructions for use of the labeling kit.

The labels and methods of the invention can be used for diagnostic and therapeutic purposes. Analytes, or combinations of analytes, that are diagnostic of a disease can be detected and quantified from a sample derived from a subject. Many different analytes can be analyzed at one time from a single sample using the methods of the invention. This allows, for example, for several diagnostic tests to be performed on one sample. In addition, the methods of the invention can provide information that determines a course of treatment for a patient. For example, the amount of a particular marker for a tumor can be accurately quantified from even a small sample from a patient. For some disease like breast cancer overexpression of certain genes, such as Her2-neu, indicate a more aggressive course of treatment will be needed.

It is understood that modifications which do not substantially affect the activity of the various embodiments of this invention are also included within the definition of the invention provided herein. Accordingly, the following examples are intended to illustrate but not limit the present invention.

Example I

Generation of Unique Labels Using Two Different Labels

In this example, ten unique labels are made from two different fluorescent labels. First, ten unique templates of a 220-base pair single-stranded DNA are synthesized. The templates consist of a pre-determined ratio of the following 20-base pair repeats: (SEQ ID NO:1) 5' (ACTCTCTCTCTCTCTCTCTC)n (GCTCTCTCTCTCTCTCTCTC)m 3' (SEQ ID NO: 2) where n=1, 2, 3, 4, 5, 6, 7, 8, 9, 10, m=1, 2, 3, 4, 5, 6, 7, 8, 9, 10, and n+m=11.

The second strand is synthesized using the primer GAGA-GAGAGA (SEQ ID NO: 3), Klenow polymerase, DNA ligase, dGTP, DATP, dUTP-fluorescein and dCTP-rhodamine. After the reaction is complete the product is treated with S1 nuclease to digest the DNA with gaps, and the remaining full length DNA is then purified. The labeled nucleotides will be incorporated into the DNA in a unique ratio determined by the ratio of the two repeats. The end result is ten uniquely labeled nucleic acids where the set ratio of fluorescein to rhodamine is 1:10, 2:9, 3:8, 4:7, 5:6, 6:5, 7:4, 8:3, 9:2, and 10:1.

A linker oligonucleotide is ligated to the labeled DNA and then this linker is used to attach the labeled DNA to the branches of a dendrimer. The dendrimer has an oligonucleotide tag of 5 bases at the stem to facilitate binding of an anti-genedigit (see Example II) and tags of 10-base pairs at the branches to facilitate binding of labeled DNA.

Example II

Generation of a Labeled Specifier

The specifiers are synthesized by ligating together one target specific sequence (synthetic oligonucleotide, peptide-nucleic acid (PNA), PCR product, or linked-nucleic acid (LNA)), and several "genedigits" (see FIG. 1A). In this example, each specifier contains a unique combination of 4 different genedigits. This results in the generation of 10,000 possible unique specifiers.

Figure 1B:
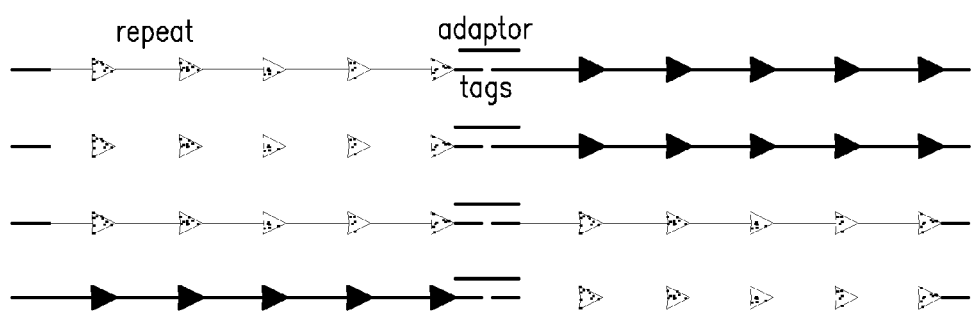
FIG. 1B shows a structure of a genedigit.

The genedigits are synthetic oligonucleotides that contain only two of the natural bases, plus two bases that not found in nature: isocytidine and isoguanine. Such base composition ensures that the genedigits will not non-specifically hybridize with analytes in a complex mixture. The sequence of each genedigit is composed of 5 repeats of an 8-base pair core sequence (see FIG. 1B). Each core sequence unit differs from the others by at least two bases.

In order to make 10,000 unique specifiers, forty different genedigits are synthesized and split into 4 groups containing 10 genedigits each. The genedigits of each group have a 5-base pair tag on each end. One genedigit from each group is present in each specifier. The genedigits are ligated with the help of adapter 10mer oligonucleotides that are complimentary to the 5-base pair tags that are common for each group. In this way, for a specifier with 4 genedigits, there will be 10×10×10×10=10,000 possible combinations. All specifiers also contain a biotin tag.

The genedigit serves as an attachment point for a label and so the number of labels synthesized corresponds to the number of genedigits. The genedigits are labeled through the use of anti-genedigits. An anti-genedigit sequence consisting of three 8-base pair repeats complimentary to the 8-base pair core repeat of the corresponding genedigit is ligated to the stem of a labeled dendrimer (from Example I).

Figure 1C:
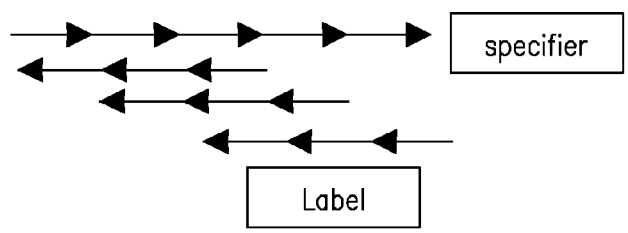
FIG. 1C shows an association between a genedigit and labeled anti-genedigit.

The 24-base pair labeled anti-genedigit hybridizes to the 40-base pair genedigit sequence in the specifier in one of three different registers (see FIG. 1C). Thus when the label hybridized to the specifier it will do so through a 24-base pair sequence that only has a complexity of an 8-base pair sequence.

Example III

Gene Expression Analysis Using Specifiers

In order to determine differences in gene expression between astrocytes and LPS-activated astrocytes, RNA is isolated from both populations of astrocytes using cell lysis in guanidine isothiocynine or phenol/chloroform. A population of specifiers is added to each RNA sample under conditions suitable for hybridization. The mRNA-specifier complexes are isolated with oligo dT beads and washed extensively to remove excess specifiers. The specifiers are eluted from the mRNA by digesting the mRNA with RNAse A. The specifiers are then are processed for labeling as described in Examples I and II and these labels are detected using a CCD camera. The number of specifiers corresponding to specific mRNAs from un-treated astrocytes is then compared to the specifier pattern from LPS-treated astrocytes. Since the sequence of the target specific region of the specifier is known, this identifies the genes that are differentially expressed between the two samples.

Example IV

Microbial Detection Using Specifiers

The invention can be used to detect strains of microorganisms with known sequence in biological samples. Total DNA is extracted from a blood sample from a patient with a suspected microbial infection. The total DNA is then tagged with digoxygenin. The DNA is denatured and hybridized with a population of specifiers containing target regions specific for a particular microorganism, or a panel of microorganisms, in a small volume (0.01-2.0 µl). The sample DNA-specifier complexes are isolated using anti-digoxygenin antibodies, and washed extensively to remove excess specifiers. The specifiers are then processed for labeling and imaging as described above.

Example V

Label Configurations

Figure 2:
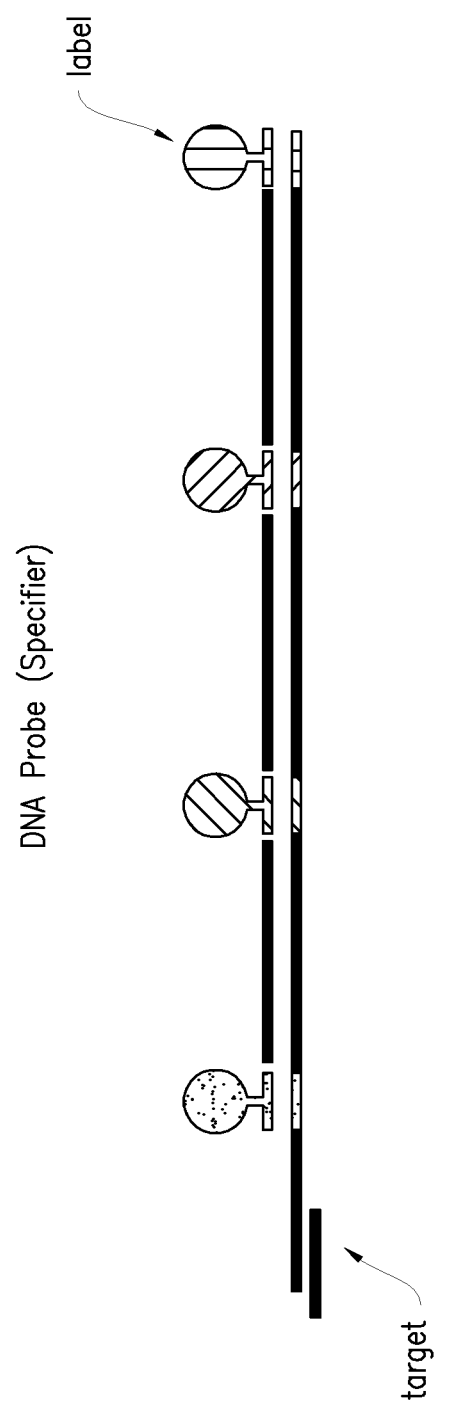
FIG. 2 shows a DNA probe molecule (specifier) that contains several different types of spatially separated labels.

This example shows a DNA probe molecule (specifier) that contains labels that are separated by a distance sufficient such that the labels can be individually resolved (FIG. 2). For example, in the case of fluorescent labels, this large spatial separation of labels allows for spectral identification of each label individually.

As shown in FIG. 2, a DNA probe (specifier) can be generated that contains four distinct fluorescent labels. These labels are separated by a distance of about one micron. In this example, the labels are separated by about 2,000 to 3,000 bases of DNA, however other polymers could be used to separate the labels as well.

A diverse population of unique labels can be generated by varying the fluorescent label at each of the four locations. For example, a set of 10 distinct fluorophores can be used to generate 10,000 unique labels. Specifically, for a probe with four different labels, there will be 10×10×10×10=10,000 possible combinations. Similarly, for a probe that has five different labels, there will be 100,000 possible combinations.

Example VI

Flow-Stretch Separation of Labels

This example shows a DNA probe molecule (specifier) with one label monomer which has been stretched on a coverslip using a flow stretch technique. The flow stretch technique can also be used for a probe molecule with multiple label monomers along the probe molecule.

Figure 3:
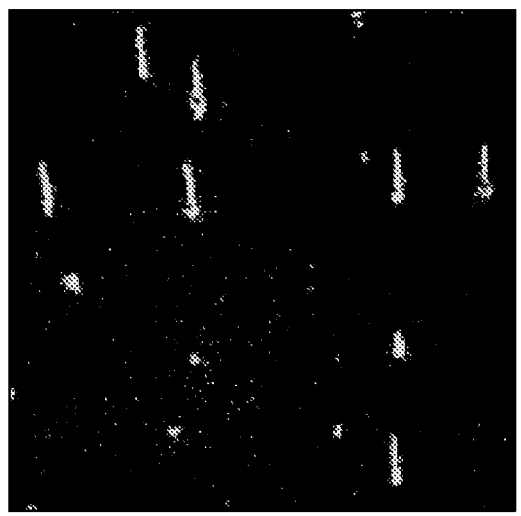
FIG. 3 shows DNA probe molecules containing a label on one end that have been stretched on a coverslip using a flow-stretch technique.

A double stranded DNA probe was constructed with a single stranded section at a desired location for label attachment. In this example, the single stranded section is at the end of the probe molecule. The label molecule contains about 300 Cy3 fluorophores and a section of DNA that is complementary to the single stranded area of the probe molecule. After hybridization, the probe molecule is stained with YOYO1 dye to verify that the label is attached to the probe. The staining procedure is not necessary when multiple labels are attached. The probes with hybridized label were then stretched on a coverslip using a flow stretch technique (Henegariu et al., supra). An image, FIG. 3, was obtained using an inverted fluorescent microscope. Probes can also be stretched using a receding meniscus technique (Yokota et al., supra).

Example VII

Electro-Stretch Separation of Labels

This example shows than an electric field can be used to align probe (specifier) molecules that are attached by one end to a surface. In this manner, labels that are along the probe molecule are spatially separated.

Figure 4A:
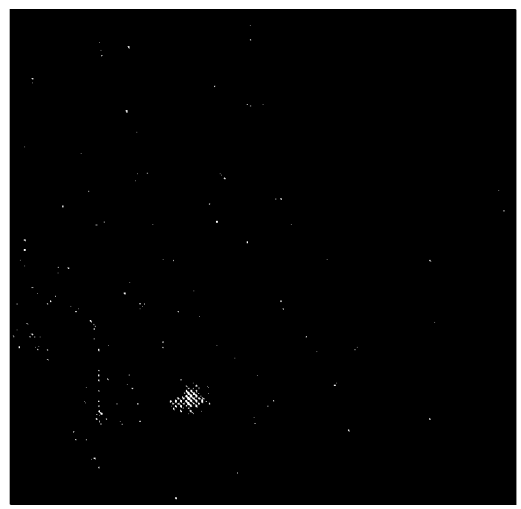
FIG. 4A shows labeled DNA probe molecules in a flow cell with the voltage off.
Figure 4B:

A flow cell was constructed that allowed imaging of the probe molecules through a coverslip. The flow cell also allowed for the exchange of solutions and the application of an electric field. In order to prevent bubbling, a gel was used to separate the electrodes from the solution. With gel separation of the electrodes and solution, higher voltages are possible which improves the alignment of the probe molecules. The coverslip was coated with bovine serum albumin (BSA) to minimize non-specific binding. DNA was added to the coverslip and attached to the coverslip primarily by the ends of the DNA. Un-bound DNA was washed away and the remaining bound DNA was stained with YOYO1. Imaging was performed using an epi-fluorescent microscope. When the voltage was off, tethered DNA can be seen to move randomly (FIG. 4A). However, when the voltage is on, the DNA becomes aligned (FIG. 4B).

Example VIII

Cytometer Detection of Labels

Figure 5:
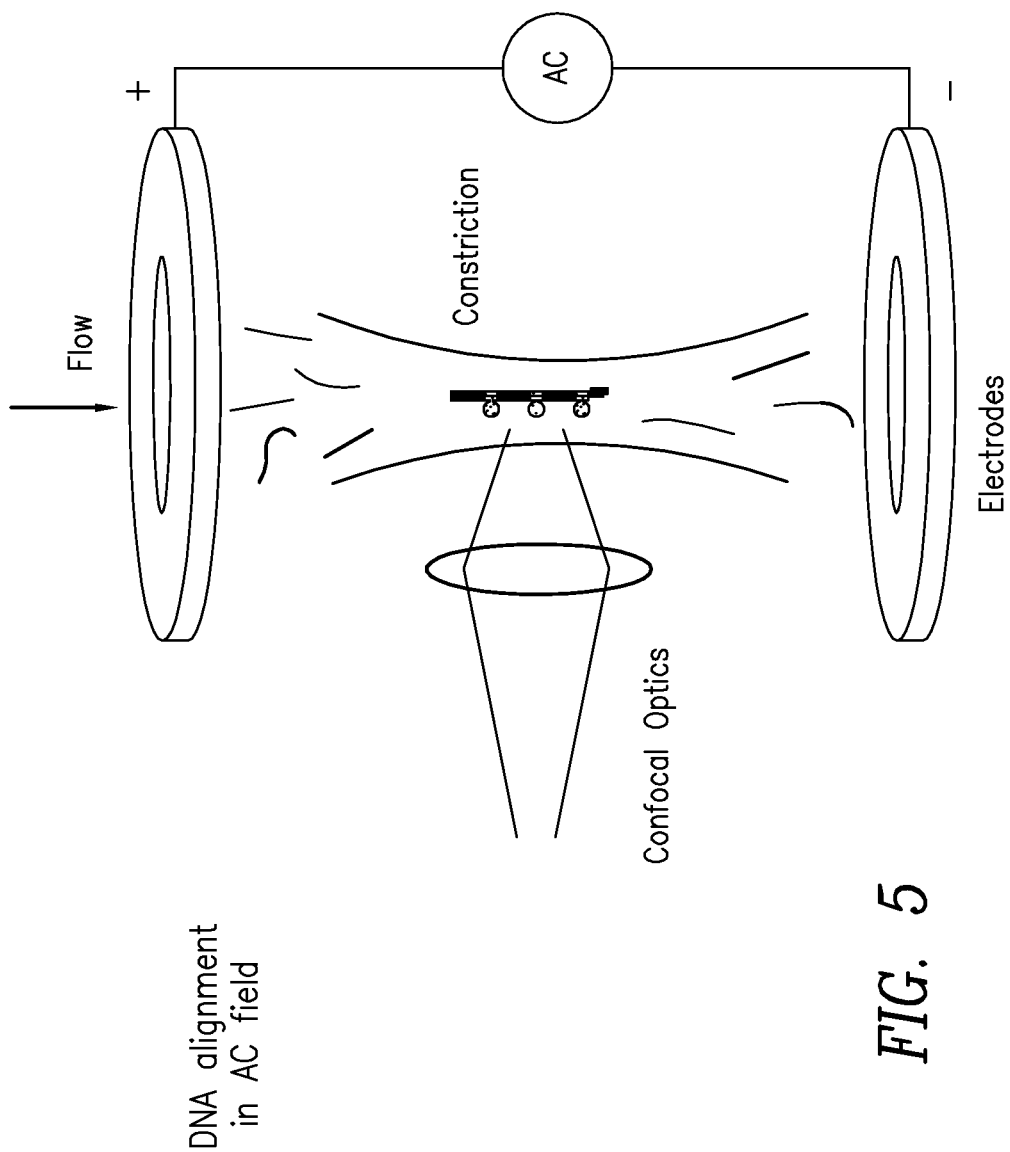
FIG. 5 shows a schematic of probes being aligned by constriction in the flow of a liquid containing the probes in the presence of an oscillating electric field.

Another way to align DNA probes (specifiers) spatially is by the use of a constriction in the flow of a liquid containing the DNA in conjunction with an oscillating electric field (Asbury, C. L., and van den Engh, G., Biophys. J. 74:1024-1030 (1998)). In this way, when the probe molecules pass through the constriction the labels are spatially separated (FIG. 5). Confocal optics can allow for detection with enough spatial resolution to determine the sequence of the labels.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:

1. A composition comprising:
   (a) a first probe comprising
      (i) a region that selectively binds to a first target specific sequence of a nucleic acid analyte, and
      (ii) a region comprising a plurality of label-attachment positions linked together, each label-attachment position being of a predetermined nucleotide sequence, wherein at least two of the label-attachment positions comprise a repeated core element, and wherein
         a first label-attachment position is attached to a complementary nucleic acid sequence comprising a first plurality of label monomers, wherein the first plurality of label monomers comprises a first label; and
         at least a second label-attachment position is attached to at least a second complementary nucleic acid sequence comprising at least a second plurality of label monomers, wherein the second plurality of label monomers comprises at least a second label;
      wherein the first label and the second label are spatially-separable for resolution of the first label from the second label; and
   (b) a second probe comprising
      (i) a region that selectively binds to a second target specific sequence of the nucleic acid analyte, wherein the first target-specific sequence and the second target-specific sequence bind to different regions of the same nucleic acid analyte, and
      (ii) an affinity tag.

2. The composition of claim 1, wherein the first probe further comprises an affinity tag.

3. The composition of claim 1, wherein the affinity tag is a biotin tag.

4. The composition of claim 2, wherein the affinity tag is a biotin tag.

5. The composition of claim 1, wherein the complementary nucleic acid sequence is DNA.

6. The composition of claim 1, wherein the complementary nucleic acid sequence is RNA.

7. The composition of claim 1, wherein the complementary nucleic acid sequence is a dendrimer.

8. The composition of claim 1, wherein the plurality of label-attachment positions comprises at least four label-attachment positions.

9. The composition of claim 1, wherein the plurality of label-attachment positions are in a predetermined order within the probe.

10. The composition of claim 1, wherein at least two of the label-attachment positions have different nucleotide sequences.

11. The composition of claim 1, wherein each label-attachment position has a different nucleotide sequence.

12. The composition of claim 11, wherein the nucleotide sequence of each label-attachment position differs by at least two nucleotides.

13. The composition of claim 1, wherein the label-attachment positions are directly linked.

14. The composition of claim 1, wherein the label-attachment positions are linked via intervening or adapting sequences.

15. The composition of claim 1, wherein each label monomer comprises a fluorescent moiety.

16. The composition of claim 1, wherein the affinity tag is a digoxigenin tag.

17. The composition of claim 2, wherein the affinity tag is a digoxigenin tag.

* * * * *

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: DNA repeat

<400> SEQUENCE: 1
actctctctc tctctctctc                                              20

<210> SEQ ID NO 2
<211> LENGTH: 20
<212> TYPE: DNA
<213> ORGANISM: Artificial Sequence
<220> FEATURE:
<223> OTHER INFORMATION: DNA repeat

<400> SEQUENCE: 2
gctctctctc tctctctctc                                              20

<210> SEQ ID NO 3
<211> LENGTH: 10
<212> TYPE: DNA
<213> ORGANISM: Artificial Sequence
<220> FEATURE:
<223> OTHER INFORMATION: Primer sequence

<400> SEQUENCE: 3
gagagagaga                                                         10
```